(12) United States Patent
Hines

(10) Patent No.: US 9,585,670 B2
(45) Date of Patent: *Mar. 7, 2017

(54) EXCLUSION DEVICE AND SYSTEM FOR DELIVERY

(71) Applicant: Electroformed Stents, Inc., Stilwell, KS (US)

(72) Inventor: Richard A. Hines, Stilwell, KS (US)

(73) Assignee: Electroformed Stents, Inc., Stilwell, KS (US)

(*) Notice: Subject to any disclaimer, the term of this patent is extended or adjusted under 35 U.S.C. 154(b) by 63 days.

This patent is subject to a terminal disclaimer.

(21) Appl. No.: 14/466,739

(22) Filed: Aug. 22, 2014

(65) Prior Publication Data

US 2014/0364895 A1 Dec. 11, 2014

Related U.S. Application Data

(62) Division of application No. 11/747,899, filed on May 12, 2007, now abandoned.

(Continued)

(51) Int. Cl.
*A61B 17/08* (2006.01)
*A61B 17/12* (2006.01)
(Continued)

(52) U.S. Cl.
CPC .. *A61B 17/12113* (2013.01); *A61B 17/12022* (2013.01); *A61B 17/12031* (2013.01);
(Continued)

(58) Field of Classification Search
CPC ........ A61B 17/12022; A61B 17/12113; A61B 17/12172; A61B 2017/1205;
(Continued)

(56) References Cited

U.S. PATENT DOCUMENTS 5,213,576 A  5/1993  Abiuso et al.
6,007,573 A  12/1999  Wallace
(Continued)

FOREIGN PATENT DOCUMENTS

WO  2006034153  3/2006

OTHER PUBLICATIONS

International Search Report for International (PCT) Application No. PCT/US07/68826, mailed Sep. 9, 2008.

(Continued)

*Primary Examiner* — Katherine M Shi
(74) *Attorney, Agent, or Firm* — Fish & Richardson P.C.

(57) ABSTRACT

A medical flow restrictor that may be used to exclude a saccular aneurysm from the circulatory system. The device, a thin walled, foil-like shell, is compacted for delivery. The invention includes the device, electroforming fabrication methods, delivery assemblies, and methods of placing, and using, the device. A device with an aneurysm lobe and an artery lobe self-aligns its waist at the neck of an aneurysm as the device shell is pressure expanded. Negative pressure is used to collapse both the aneurysm lobe and the artery lobe, captivating the neck of the aneurysm and securing the device. The device works for aneurysms at bifurcations and aneurysms near side-branch arteries. The device, unlike endovascular coiling, excludes the weak neck of the aneurysm from circulation, while leaving the aneurysm relatively empty. Unlike stent-based exclusion, the device does not block perforator arteries. This exclusion device can also limit flow through body lumens or orifices.

6 Claims, 18 Drawing Sheets

Related U.S. Application Data

(60) Provisional application No. 60/855,872, filed on Nov. 1, 2006, provisional application No. 60/799,758, filed on May 12, 2006.

(51) Int. Cl.
   *B05D 3/00* (2006.01)
   *C25D 1/02* (2006.01)
   *A61B 17/00* (2006.01)

(52) U.S. Cl.
   CPC .. *A61B 17/12136* (2013.01); *A61B 17/12172* (2013.01); *B05D 3/007* (2013.01); *C25D 1/02* (2013.01); *A61B 2017/00526* (2013.01); *A61B 2017/1205* (2013.01); *A61B 2017/12054* (2013.01)

(58) Field of Classification Search
   CPC .... A61B 17/12136; A61B 2017/12054; A61B 17/0057; A61B 2017/12063
   USPC ................................ 606/151, 194, 195, 200
   See application file for complete search history.

(56) References Cited

U.S. PATENT DOCUMENTS

| | | | |
|---|---|---|---|
| 6,019,784 A | 2/2000 | Hines | |
| 6,080,191 A | 6/2000 | Summers | |
| 6,270,515 B1 | 8/2001 | Linden et al. | |
| 6,274,294 B1 | 8/2001 | Hines | |
| 6,350,270 B1 | 2/2002 | Roue | |
| 6,454,780 B1 | 9/2002 | Wallace | |
| 6,463,317 B1 | 10/2002 | Kucharczyk et al. | |
| 6,506,204 B2 | 1/2003 | Mazzocchi | |
| 6,527,919 B1 | 3/2003 | Roth | |
| 6,547,804 B2 | 4/2003 | Porter et al. | |
| 6,569,190 B2 | 5/2003 | Whalen, II et al. | |
| 6,669,719 B2 | 12/2003 | Wallace et al. | |
| 6,689,159 B2 | 2/2004 | Hartigan et al. | |
| 6,811,560 B2 | 11/2004 | Jones et al. | |
| 6,855,154 B2 | 2/2005 | Abdel-Gawwad | |
| 6,904,658 B2 | 6/2005 | Hines | |
| 6,969,401 B1 | 11/2005 | Marotta et al. | |
| 7,147,659 B2 | 12/2006 | Jones | |
| 7,156,871 B2 | 1/2007 | Jones et al. | |
| 7,293,562 B2 | 11/2007 | Malecki et al. | |
| 2002/0082638 A1* | 6/2002 | Porter .............. A61B 17/12113 606/195 |
| 2002/0143349 A1 | 10/2002 | Gifford et al. | |
| 2002/0165569 A1* | 11/2002 | Ramzipoor ...... A61B 17/12022 606/191 |
| 2003/0028210 A1 | 2/2003 | Boyle et al. | |
| 2003/0120337 A1 | 6/2003 | Van Tassel et al. | |
| 2003/0181927 A1 | 9/2003 | Wallace | |
| 2004/0034386 A1 | 2/2004 | Fulton et al. | |
| 2004/0044391 A1 | 3/2004 | Porter | |
| 2004/0167597 A1 | 8/2004 | Costantino | |
| 2005/0021016 A1 | 1/2005 | Malecki et al. | |
| 2006/0052816 A1* | 3/2006 | Bates ............... A61B 17/12013 606/200 |
| 2006/0064151 A1 | 3/2006 | Guterman et al. | |
| 2006/0136043 A1 | 6/2006 | Cully et al. | |
| 2006/0155367 A1 | 7/2006 | Hines | |
| 2006/0167494 A1 | 7/2006 | Suddaby | |

OTHER PUBLICATIONS

Written Opinion for International (PCT) Application No. PCT/US07/68826, mailed Sep. 9, 2008.

International Search Report for International (PCT) Application No. PCT/US07/68826, mailed Oct. 19, 2004.

Written Opinion for International (PCT) Application No. PCT/US07/68826, mailed Oct. 19, 2004.

\* cited by examiner

EXCLUSION DEVICE AND SYSTEM FOR DELIVERY

CROSS-REFERENCE TO RELATED APPLICATIONS

This application is a divisional application of U.S. Ser. No. 11/747,899 filed May 12, 2007 which claims the benefit of priority under 35 U.S.C. §119(e) to provisional application number 60/799,758 filed May 12, 2006, and to provisional application number 60/855,872, filed Nov. 1, 2006, each of which are incorporated herein by this reference.

TECHNICAL FIELD

The present invention relates to the field of medical intraluminal delivery of an implantable device that reduces or stops fluid movement that would otherwise flow or circulate through a body lumen or orifice. The invention is well suited for the treatment of neurovascular aneurysms or any other condition that could benefit by completely, or partially, excluding flow through a body orifice or vessel.

BACKGROUND OF THE INVENTION

An aneurysm forms when a dilated portion of an artery is stretched thin from the pressure of the blood. The weakened part of the artery forms a bulge, or a ballooning area, that risks leak or rupture. When a neurovascular aneurysm ruptures, it causes bleeding into the compartment surrounding the brain, the subarachnoid space, causing a subarachnoid hemorrhage. Subarachnoid hemorrhage from a ruptured neurovascular aneurysm can lead to a hemorrhagic stroke, brain damage, and death. Approximately 25 percent of all patients with a neurovascular aneurysm suffer a subarachnoid hemorrhage.

Neurovascular aneurysms occur in two to five percent of the population and more commonly in women than men. It is estimated that as many as 18 million people currently living in the United States will develop a neurovascular aneurysm during their lifetime. Annually, the incidence of subarachnoid hemorrhage in the United States exceeds 30,000 people. Ten to fifteen percent of these patients die before reaching the hospital and over 50 percent die within the first thirty days after rupture. Of those who survive, about half suffer some permanent neurological deficit.

Smoking, hypertension, traumatic head injury, alcohol abuse, use of hormonal contraception, family history of brain aneurysms, and other inherited disorders such as Ehler's syndrome, polycystic kidney disease, and Marfan syndrome possibly contribute to neurovascular aneurysms.

Most unruptured aneurysms are asymptomatic. Some people with unruptured aneurysms experience some or all of the following symptoms: peripheral vision deficits, thinking or processing problems, speech complications, perceptual problems, sudden changes in behavior, loss of balance and coordination, decreased concentration, short-term memory difficulty, and fatigue. Symptoms of ruptured neurovascular aneurysm include nausea and vomiting, stiff neck or neck pain, blurred or double vision, pain above and behind the eyes, dilated pupils, sensitivity to light, and loss of sensation. Sometimes patients describing "the worst headache of my life" are experiencing one of the symptoms of a ruptured neurovascular aneurysm.

Most aneurysms remain undetected until a rupture occurs. Aneurysms, however, may be discovered during routine medical exams of diagnostic procedures for other health problems. Diagnosis of a ruptured cerebral aneurysm is commonly made by finding signs of subarachnoid hemorrhage on a CT scan (Computerized Tomography). If the CT scan is negative but a ruptured aneurysm is still suspected, a lumbar puncture is performed to detect blood in the cerebrospinal fluid (CSF) that surrounds the brain and spinal cord.

To determine the exact location, size, and shape of an aneurysm, neuroradiologists use either cerebral angiography or tomographic angiography. Cerebral angiography, the traditional method, involves introducing a catheter into an artery (usually in the leg) and steering it through the blood vessels of the body to the artery involved by the aneurysm. A special dye, called a contrast agent, is injected into the patient's artery and its distribution is shown on X-ray projections. This method may not detect some aneurysms due to overlapping structures or spasm.

Computed Tomographic Angiography (CTA) is an alternative to the traditional method and can be performed without the need for arterial catheterization. This test combines a regular CT scan with a contrast dye injected in a vein. Once the dye is injected into a vein, it travels to the brain arteries, and images are created using a CT scan. These images show exactly how blood flows into the brain arteries. New diagnostic modalities promise to supplement both classical and conventional diagnostic studies with less-invasive imaging and possibly provide more accurate 3-dimensional anatomic information relative to aneurismal pathology. Better imaging, combined with the development of improved minimally invasive treatments, will enable physicians to increasingly detect, and treat, more silent aneurysms before problems arise.

Currently, neurovascular aneurysms are treated via a limited range of methods. The potential benefits of current aneurismal treatments often do not outweigh the risks, especially for patients whose remaining life expectancy is less than 20 years.

The original aneurysm treatment, neurosurgical clipping, a highly invasive and risky open surgery, remains the most common treatment for neurovascular aneurysms. Under general anesthesia, a surgeon performs a craniotomy, the removal of a section of the skull, gently retracts the brain to locate the aneurysm, and places a small clip across the base, or neck, of the aneurysm, blocking the normal blood flow from entering the aneurysm. After completely obliterating the aneurysm with the tiny metal clip, the surgeon secures the skull in its original place and closes the wound. The risk of a craniotomy, including the potential for further injury to the brain and additional neurological defect, are exacerbated in patients with a recent brain injury as well as in elderly or medically complicated patients.

In 1995, following the pioneering work of Dr. Fernando Vinuela and Dr. Guido Guglielmi, the FDA approved an endovascular aneurismal treatment: "coiling." In this procedure, an interventional radiologist guides a catheter from the femoral artery, through the aorta, and into the cerebral vasculature, via either the carotid or vertebral artery, until it reaches the aneurysm. Embolic coils, small spring-like devices typically made of platinum, are then threaded through the catheter and packed into the aneurysm until enough coils are present to limit blood flow into the aneurysm. This process, embolization, works by reducing blood circulation in the aneurysm, thereby triggering a thrombus. By converting liquid blood into a solid, coils reduce the danger of the aneurysm leaking or rupturing.

The introduction and continued evolution of the endovascular coiling process has certainly advanced less-invasive aneurismal treatment, but the coiling process has limitations. Strong forces, generated by interluminal flow around and into the aneurysm, often compacts, shifts, or partially dislodges the volume of coils left in the aneurysm. A portion of a coil that prolapses out of the aneurysm neck can lead to serious and adverse consequences (e.g. clot formation, calcification, or other hardening and filling of the artery), and create difficulties in reaching the aneurysm for future treatment.

Recanalization, the reformation of an aneurysm at its neck, occurs in approximately 15 percent of coiled aneurysms and in nearly 50 percent of coiled "giant" aneurysms. Since coiling does not protect the neck of the aneurysm, a coiled aneurysm risks recanalization, which may lead to future rupture and the need for repeat treatment(s). Furthermore, coils create what is known as the mass effect: the permanent lump of coils contained within the aneurysm that maintain an undesirable pressure on the surrounding brain tissue.

The coiling process only works effectively in some aneurysms, specifically small-necked aneurysms where the coils are more likely to stay securely in place within the aneurysm. In wide or medium-necked aneurysms, coils may protrude or prolapse into the parent vessel and create a risk of clot formation and embolism.

In order to combat this design deficit, physicians have begun using stents to improve the effectiveness of coiling. With stent-assisted coiling, a stent lines the arterial wall, creating a screen that secures the coils inside the aneurysm. These stents are generally self-expanding and have a low surface density to make them deliverable. Thus, the stent itself does not limit flow into the aneurysm sufficiently to trigger a thrombus in the aneurysm. However, even these low surface density stents run a significant risk of blocking perforator arteries, creating unpredictable damage to other parts of the brain. Additionally, any stent in the parent artery creates a risk of clot formation in the artery.

To prevent these dangers, the use of an implantable device that covers only the neck of the aneurysm with a greater percent solid area would more effectively restrict blood circulation into the aneurysm, trigger a thrombus (the solidification of liquid blood within the aneurysm), and eliminate the danger of leak or rupture. Ideally, after formation of the thrombus, aneurismal sac will shrink as the thrombus is absorbed, further reducing the chance of leak or rupture of the aneurysm, while also reducing pressure on the surrounding tissue. Coils or other devices which remain in the aneurysmal sac tend to maintain the original aneurysm volume, and thus the aneurysm continues to exert pressure on the surrounding tissue.

Several additional types of devices designed to limit blood flow into an aneurysm have been described previously, yet none have been commercialized, or approved by the FDA. In these methods, blood flow into the aneurysm is limited to the degree necessary to form a thrombus in the aneurysm without filling the aneurysm with coils, a solidifying agent, or other introduced matter. This type of solution often uses a stent, or stent-like device, in the parent artery. However, unlike stents used to hold coils in place, the surface density of these stents sufficiently limit blood flow into the aneurysm and encourage thrombus formation. For example, U.S. Pat. Nos. 6,527,919; 6,080,191; 6,007,573; and 6,669,719 discuss stents that use methods involving rolled, flat sheets, and U.S. Pat. No. 6,689,159 discusses a radially expandable stent with cylindrical elements where expansion occurs when the stress of compression is removed. Most stents manufactured with a high-percent solid area have limited longitudinal flexibility, tend to have a large delivery diameter, and have an unacceptable probability of blocking perforator arteries, and thus limiting the number of aneurysms they can reach and treat. Additionally, since these methods require a straight parent artery, they will not work at the primary location of most aneurysms: bifurcations, the division of a single artery into two branches. The micro-pleated stent assembly of U.S. Patent Publication No. 2006-0155367 by Hines describes a stent for endovascular treatments that has many advantages over other methods of treating aneurysms. However, this high surface area stent cannot be used to treat aneurysms near side branch or perforator arteries. Even though a micro-pleated, or other neurovascular stent can be patterned with a relatively dense patch area designed to cover the neck of the aneurysm, a micro-pleated stent, or other thin-strutted device that covers artery surface beyond the aneurismal neck, runs a significant, and often unpredictable, risk of restricting blood flow to a smaller, branch artery.

Other methods that artificially solidify aneurysms have been described previously. For example, U.S. Pat. No. 6,569,190 discloses a method for treating aneurysms that fills the aneurismal sac with a non-particulate agent, or fluid, that solidifies in situ. This process leaves an undesirable side effect: a permanent, solidified lump cast in the volume of the aneurysm. The filling agent also risks leaking, or breaking off into, the parent artery, thereby creating a risk of embolus formation.

Previously described methods fill the aneurismal sac with a device or portion of a device. For example, U.S. Patent Publication No. 2006-0052816 by Bates et al., describes a device for treating aneurysms using a basket-like device within the aneurysm that engages the inner surface of the aneurysm and blocks flow into the aneurysm. Similarly, U.S. Pat. No. 6,506,204 by Mazzocchi fills the aneurysm with a wire mesh device that also attempts to captivate the neck of the aneurysm. The devices described by Bates et al., Mazzocchi, and similar devices do not allow the aneurysm volume to shrink and therefore do not lessen pressure on surrounding brain tissue. Such devices depend on an accurate fit within the inner geometry of the aneurismal sac, which is usually quite irregular and difficult to determine, even with advanced imaging techniques. If sized inaccurately, these devices will not completely fill the aneurysm nor seal the neck of the aneurysm, causing recanalization of the aneurysm from the strong lateral forces of the blood. The Mazzocchi device provides no possibility of contouring the part of the device that remains in the parent artery to the arterial wall. Even the smallest amount of material extending into the parent artery runs an unacceptable risk of clot formation and resulting embolism. The Bates et al. device does not adequately protect the aneurysm neck, which may cause an unwanted expansion of the aneurismal neck and sac that risks leak or rupture. Due to these described limitations, among other practical concerns, aneurysm treatment devices such as those described by Bates et al. and Mazzocchi have received virtually no commercial interest.

Other devices that bridge the neck of an aneurysm have been described. For example, U.S. Patent Publication No. 2003-0181927 by Wallace describes a neck bridge used to hold an embolic agent within the aneurysm. Wallace makes no provision to captivate the neck of the aneurysm and thus relies on filling the aneurysm with a particulate agent, liquid embolics, or coils in order to secure the device in place. This type of aneurysm treatment does not eliminate the mass effect on surrounding brain tissue. Aneurysm neck bridge solutions described previously, including Wallace, that do not permanently engage the inner surface of the aneurysm must rely on some internal, or external, means in which to hold the neck bridge in its final position. For example, U.S. Patent Publication No. 2006-0167494 by Suddaby attempts to leave some space in the aneurysmal sac that would allow the sac to shrink over time, thereby lessening the mass effect. Suddaby, and similar designs, necessarily rely on an activation mechanism or restraining means to hold the device shape after deployment. Such mechanisms concern physicians for many reasons. Specifically, their size and complexity limits usefulness in the tiny and complex neurovascular anatomy. Additionally, springs or other internal restraining mechanisms risk puncturing the extremely fragile aneurysm neck or sac, which could result in potentially disastrous consequences. Suddaby does not describe, or disclose, any mechanism that holds the device in the described deployed shape, nor does it describe how the device is disconnected from the delivery system. Suddaby fails to provide a workable design, describing a physically impossible transition from an initial delivery shape to a final deployed shape, with no explanation of the mechanisms or forces involved. The need, therefore, remains for an aneurysm exclusion device that can be reliably delivered and deployed to seal the neck of neurovascular aneurysms, in a manner that prevents recanalization of the aneurysm, that eliminates the mass effect, and that poses only a minimal risk of inflicting damage to the aneurismal sac, neck, or parent artery.

As a result of the previously stated factors, the current technologies and devices ineffectively treat most aneurysms. The present invention, however, overcomes the limitations of the current technologies and devices and thereby provides a new hope for the safe, simple, and effective treatment of aneurysms.

BRIEF SUMMARY OF THE INVENTION

The current invention details an exclusion device and endovascular catheter-based delivery system. The driver, when deployed in a lumen or orifice, reduces the flow of fluid past the device. In an illustrative embodiment, the device is delivered endovascularly to the neck of an aneurysm and deployed to block the neck of the aneurysm, thereby reducing blood flow into the aneurysm. The deployment leaves the parent artery fully open and does not block perforator arteries that may exist near the aneurysm. In addition, the present invention treats aneurysms at bifurcations and aneurysms located on the side of an artery.

The exclusion device of the present invention, a thin-walled, ductile shell, transitions between an initial as-manufactured shape, a compacted delivery shape, a pressure expanded shape similar to the as-manufactured shape, an evacuated crushed shape, and a final balloon-contoured shape. When deployed at the neck of an aneurysms, the exclusion device reduces blood circulation into the aneurysm, triggering a thrombus in the aneurysm that starts the healing process.

The novel balloon-like device is preferably an extremely thin ductile shell that includes an aneurysm lobe, a waist, and an artery lobe. The lobe/waist design, combined with the material properties of the device, insures that a vacuum collapse of the device results in the appropriate shape (i.e. the two lobes collapse onto each other and captivate the neck of the aneurysm).

For delivery, the exclusion device is attached, in an airtight fashion, to the distal end of a delivery tube. The delivery tube, which transmits the necessary pressure to expand and collapse the device, may be constructed of any material suitable for advancing the device through a catheter within a body lumen to the deployment site. Optionally, a thin, tubular protection sheath may cover the device as it is advanced to the deployment site. The protection sheath may be operably extended, through the outer catheter tube, outside the body so that the sheath may be pulled back, exposing the exclusion device prior to expansion. This release from the outer sheath may occur in controlled stages, allowing the device to be expanded one lobe at a time: the aneurysm (distal) lobe first while the sheath restrains the artery lobe.

If no protective sheath is used, an outer catheter tube may restrain the artery lobe during expansion of the aneurysm lobe. This expansion of the aneurysm lobe may aid in properly deploying the device by facilitating sealing of the expanded aneurysm lobe against the neck of the aneurysm, leaving the device in the proper position for full inflation of the artery lobe.

After expansion of both the aneurysm and artery lobes, the device is collapsed by applying vacuum pressure transmitted through the delivery tube. External pressure collapses the tow lobes, captivating the neck of the aneurysm between the two collapsed lobes.

Following disconnection of the exclusion device, the delivery tube, and any remaining hardware (with the possible exception of the guidewire), is removed. The final step in the deployment could use expansions of a balloon catheter, advanced over a guidewire, in the lumen of the artery, to push any portions of the exclusion device that may be remaining in the artery lumen, to the artery wall, completely flattening the artery lobe and stem of the device while fully opening the artery.

Unlike any other devices for treating aneurysms, the exclusion device shell manufactured according to the present invention, holds its contoured shape without any means of internal or external restraint due to the foil-like nature of its thin, ductile, metal composition. A thin, plastic exclusion device shell, or shell constructed of any material or materials that does not completely hold its balloon contoured shape flush against the arterial wall may use internal adhesion to retain its final, contoured shape.

An exclusion device, manufactured and deployed as described by this invention, may be used to treat a patient with an aneurysm which has a significant leak or which has ruptured completely. The exclusion device is able to occlude a ruptured aneurysm where significant forces exist due to flowing blood. The present invention provides a treatment option in these crucial cases because of its novel characteristics, which enable a secure, solid seal to be reliably placed over the neck of a ruptured aneurysm. Additionally, the simplicity and speed with which an exclusion device may be deployed make this invention a unique and useful treatment option. This exclusion device, once deployed across the neck of a ruptured or leaking aneurysm, provides an immediate barrier to flowing blood, with no need to wait for thrombus formation, as is the case with coiling. Additionally, coiling is usually not an option in a ruptured aneurysm due to the risk of coils migrating through the hole in the aneurysmal sac and into the brain cavity.

The exclusion device and delivery process may be used to close, or block, other body lumens or orifices. For example, the device may be used to close a Patent Foramen Ovale (PFO) or various fistulas. With minor modifications within the scope of this invention, the device may be used to temporarily, or permanently, close fallopian tubes.

Various fabrication and delivery options within the scope of this invention may be used to tailor the device for specific conditions. Overall size of the device, and the relative size and shape of the lobes and waist, may be tailored to fit the treatment of any aneurysm or defect.

BRIEF DESCRIPTION OF THE DRAWINGS

FIGS. 1-10 depict delivery system option one in which the exclusion device is compacted around, and slides over, a guidewire for delivery.

FIG. 1 shows a cross-section of an exclusion device shell and mandrel.

FIG. 2 depicts a flattened exclusion device attached in an airtight fashion to a delivery tube.

FIG. 4 depicts an exclusion device assembly in an aneurysm at an arterial bifurcation prior to inflation.

FIG. 5 depicts an exclusion device, reformed by pressure expansion, at the neck of an aneurysm.

FIG. 6 depicts an evacuated and collapsed exclusion device shell in the neck of an aneurysm.

FIG. 7 depicts a collapsed exclusion device shell following detachment from a delivery tube.

FIG. 8 depicts a balloon contouring of an exclusion device shell to an arterial wall.

FIG. 9 shows a cross-section of exclusion device shell and mandrel with bellows.

FIG. 10 depicts an exclusion device with bellows, reformed by expansion, at the neck of an aneurysm.

FIG. 11 depicts an aneurysm at a bifurcation with an inserted guidewire and an outer catheter tube advanced over a guidewire.

FIG. 12 depicts a compacted exclusion device advanced from an outer catheter tube at the neck of an aneurysm.

FIG. 13 depicts an exclusion device with an aneurysm lobe expanded in the aneurysm while at artery lobe is restrained with an outer catheter tube.

FIG. 14 depicts an exclusion device with an aneurysm lobe expanded in the aneurysm while an artery lobe is restrained with the protective sheath.

FIG. 15 depicts an exclusion device, with an expanded aneurysm lobe seated against the inner neck of an aneurysm, in position for full expansion.

FIG. 16 depicts a fully expanded exclusion device.

FIG. 17 depicts a vacuum collapsed exclusion device.

FIG. 18 depicts disconnection of an exclusion device from a delivery tube by using the distal tip of an outer catheter tube to shear shell material, leaving the stem glued to a delivery tube for removal from a body.

LIST OF REFERENCE NUMERALS

Figure 1:
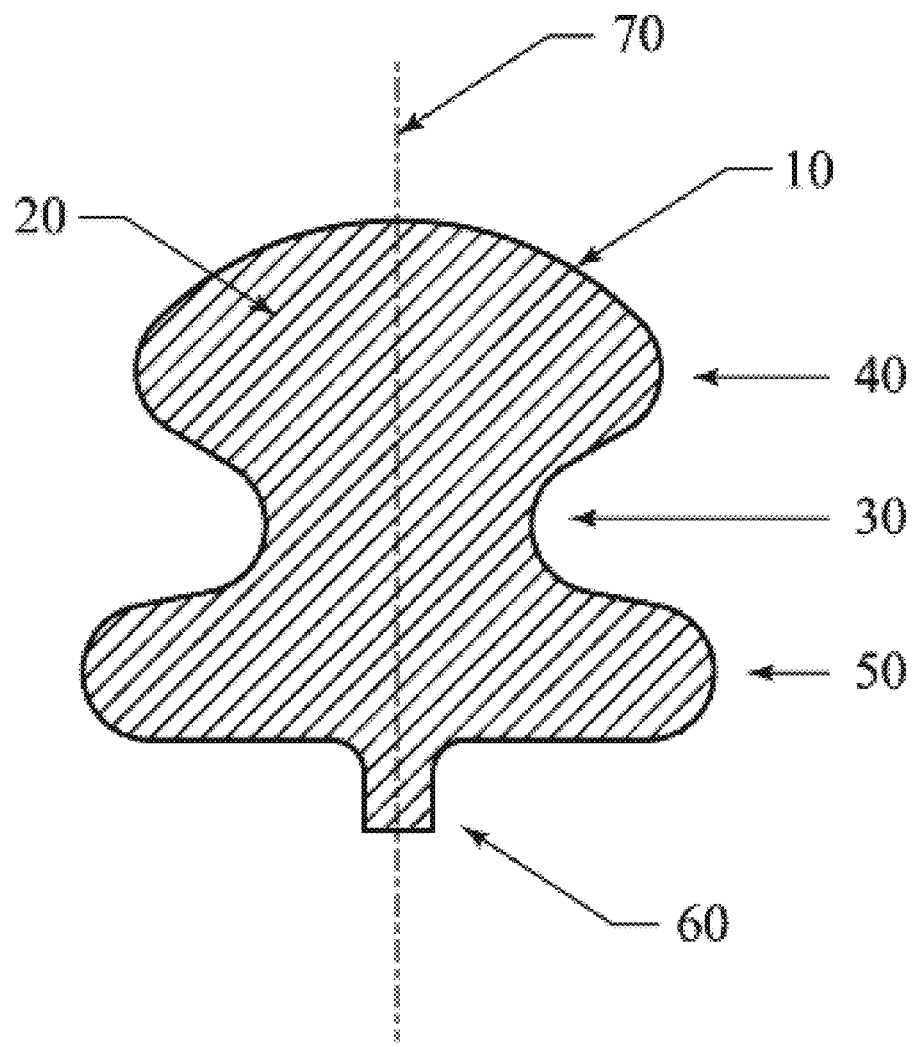

10 Exclusion device
20 Mandrel
30 Waist of exclusion device
40 Aneurysm (distal) lobe
50 Artery (proximal) lobe
60 Stem
70 Axis of rotation
80 Bellows section
110 Flattened exclusion device shell
130 Internal void
140 Folded shell
150 Rolled shell
155 Compacted exclusion device
200 Delivery tube
210 Disconnection pushed wire
220 Guidewire guide
300 Guidewire
310 Flexible tip of guidewire
410 Parent artery
420 Smaller arteries distal to a bifurcation
430 Aneurysm
435 Aneurysm neck
460 Protective sheath
500 Outer catheter tube
600 Balloon catheter

DETAILED DESCRIPTION OF THE INVENTION

The current invention provides an exclusion device and novel catheter-based endovascular delivery and deployment methods. In the illustrative embodiments depicted in FIGS. 1-18, an exclusion device 10 is delivered to an aneurysm 430, positioned at the neck 435 of the aneurysm, and deployed, thereby blocking the neck of the aneurysm and reducing blood flow into the aneurysm 430. The deployment leaves the parent (proximal) artery 410 fully open.

Figure 10:
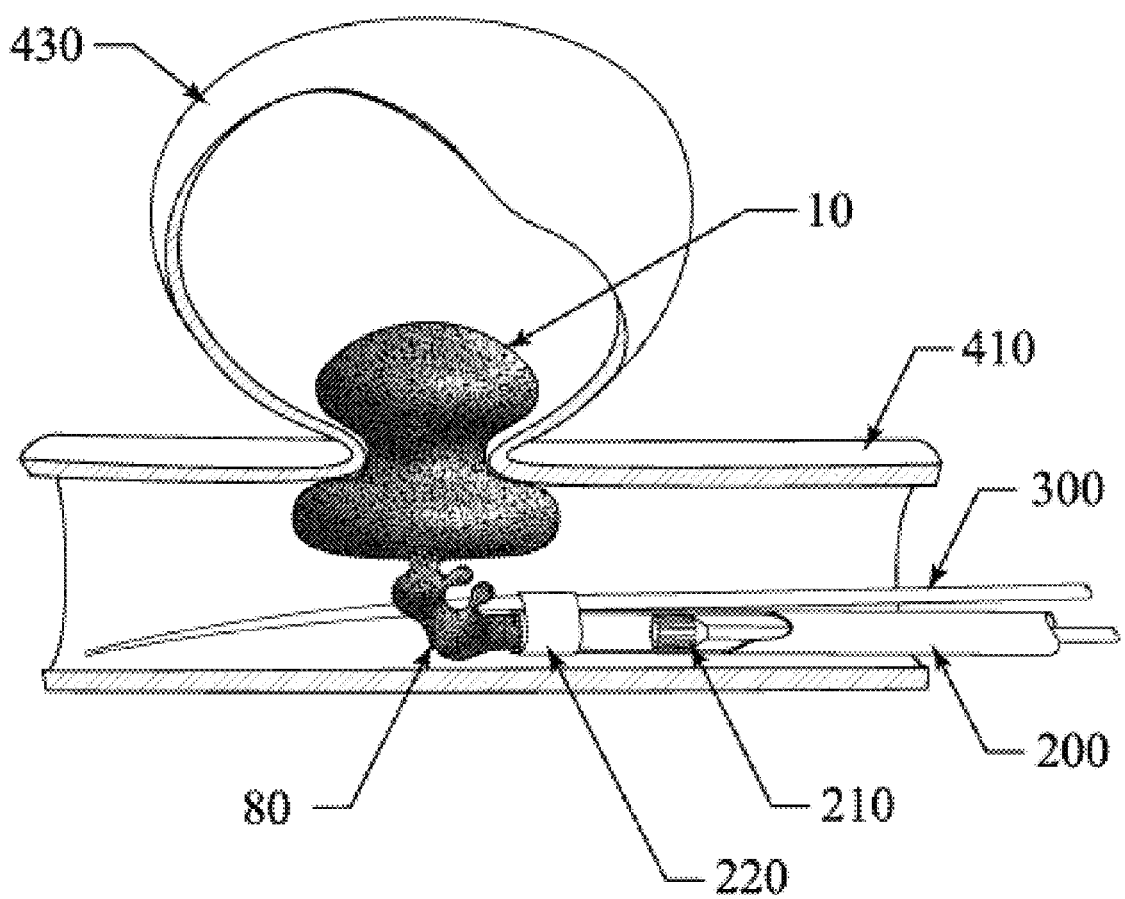
Figure 11:
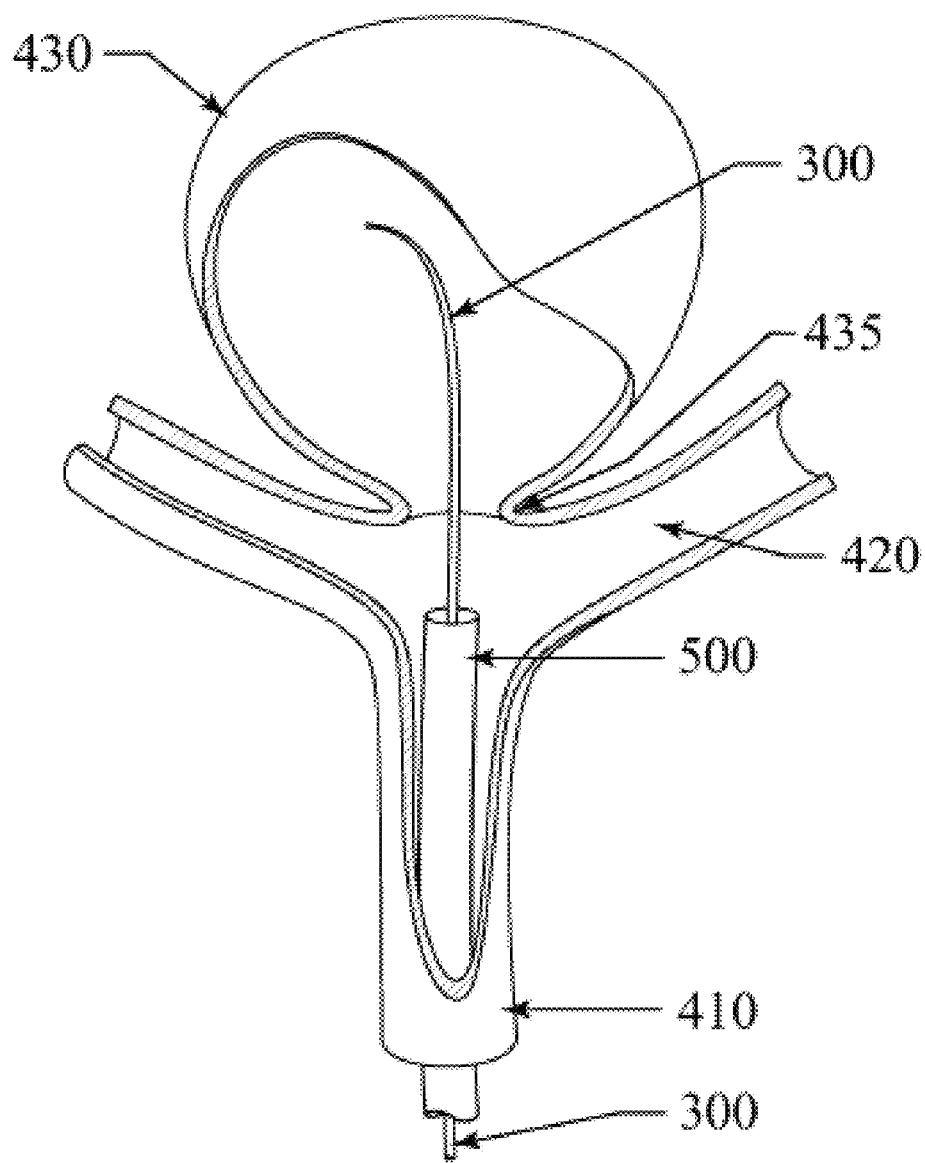
FIGS. 11-18 depict delivery system option two which uses an additional catheter tube outside a delivery tube.

At a bifurcation, the proximal artery 410 splits into two smaller arteries 420 as shown in FIGS. 4-8, and FIGS. 11-18. The deployed exclusion device does not block side branch arteries that may exist near the aneurysm. Aneurysms at bifurcations (as shown in FIGS. 4-8 and FIGS. 11-18) and aneurysms on the side of an artery (as shown in FIG. 10) may be treated. The exclusion device, deployed to cover the neck of an aneurysm, reduces blood flow into the aneurysm and triggers a thrombus in the aneurysm that starts the healing process.

Figure 3A:
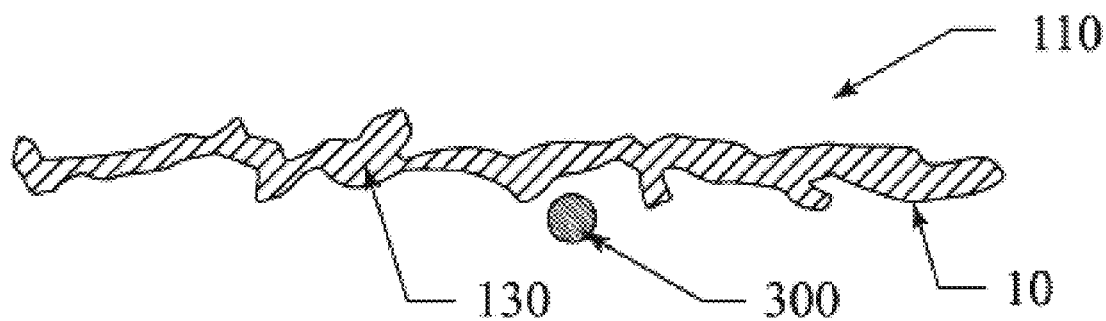
FIG. 3A shows a cross-section of a flattened exclusion device with a guidewire.
Figure 3B:
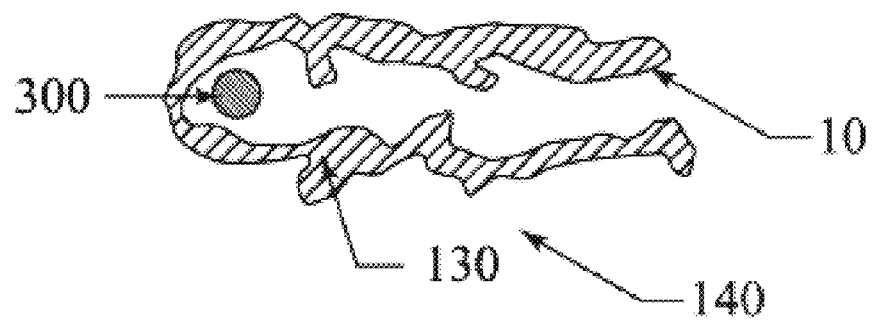
FIG. 3B shows a cross-section of a flattened exclusion device folded around a guidewire.
Figure 3C:
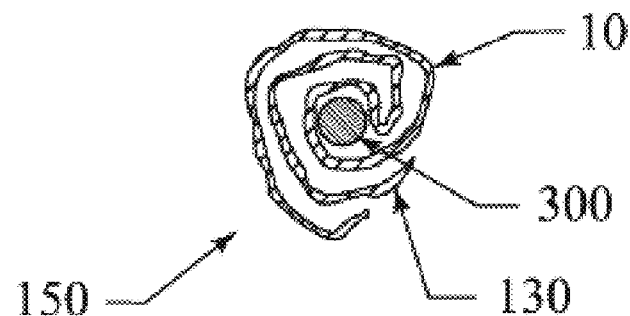
FIG. 3C shows a cross-section of a flattened exclusion device rolled around a guidewire.
Figure 4:
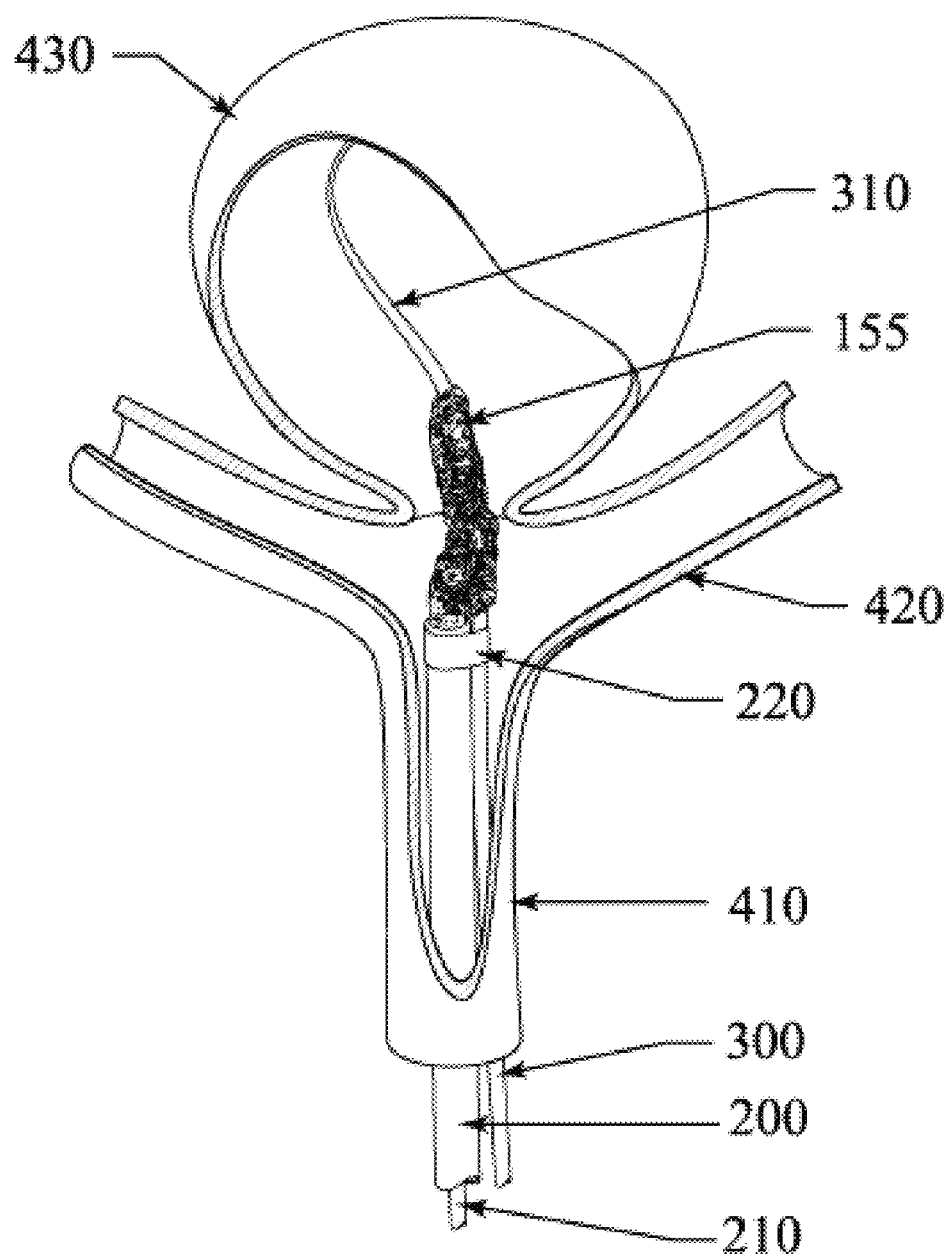
Figure 5:
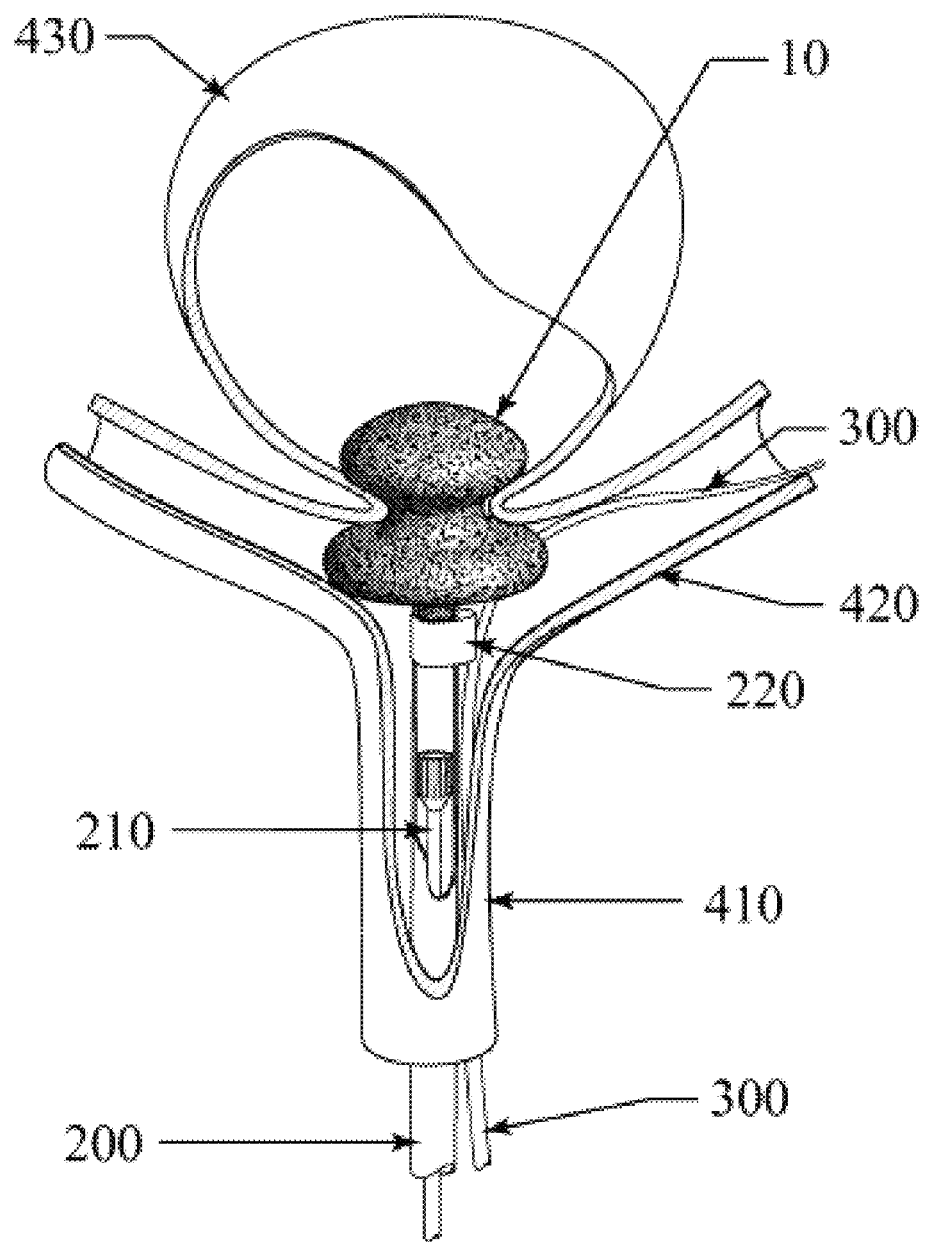
Figure 8:
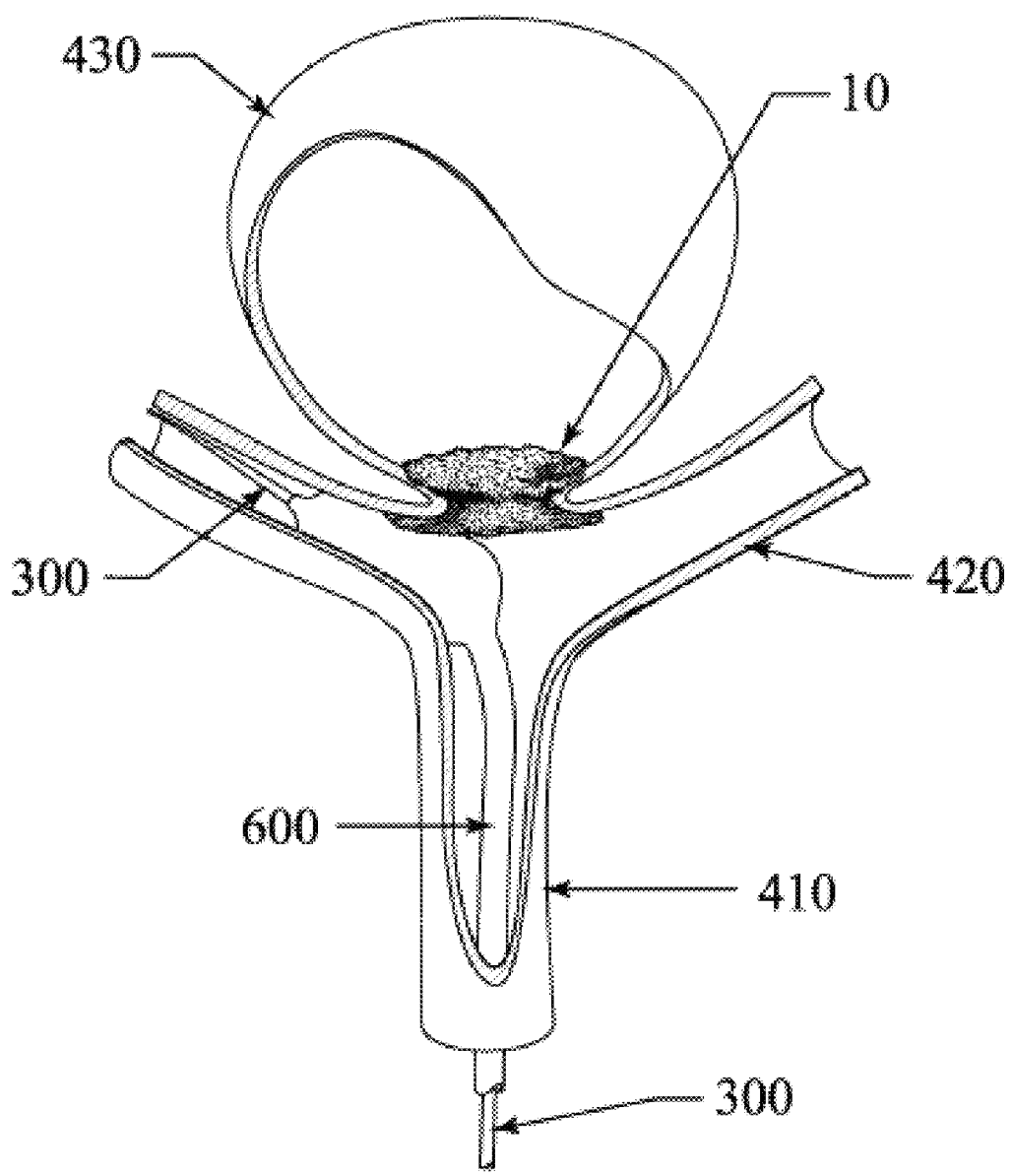
Figure 9:
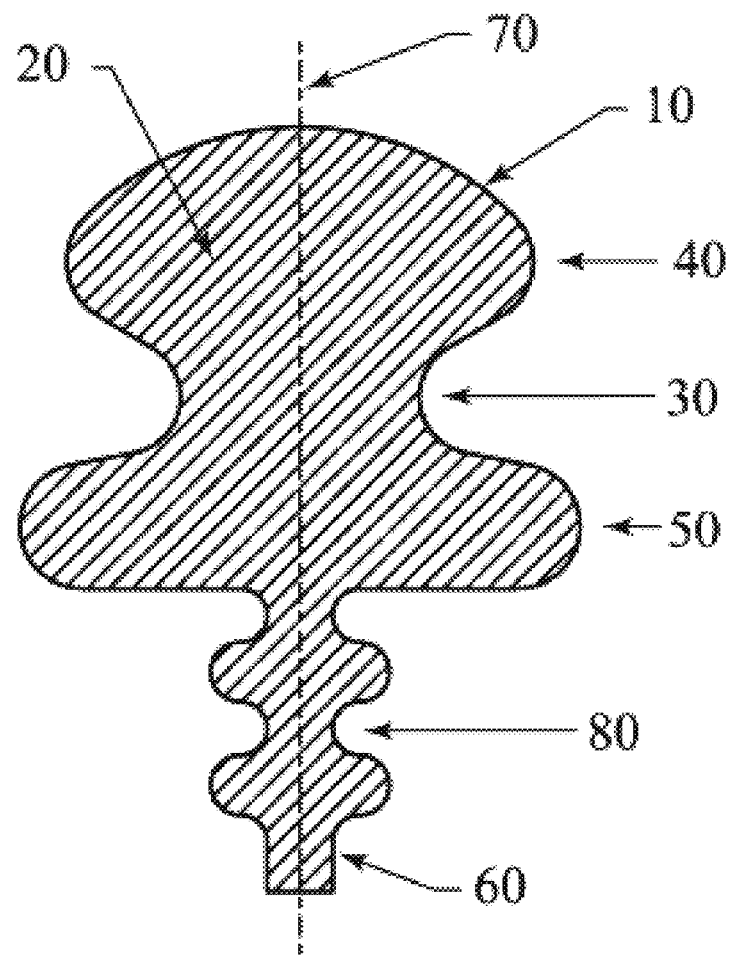
Figure 12:
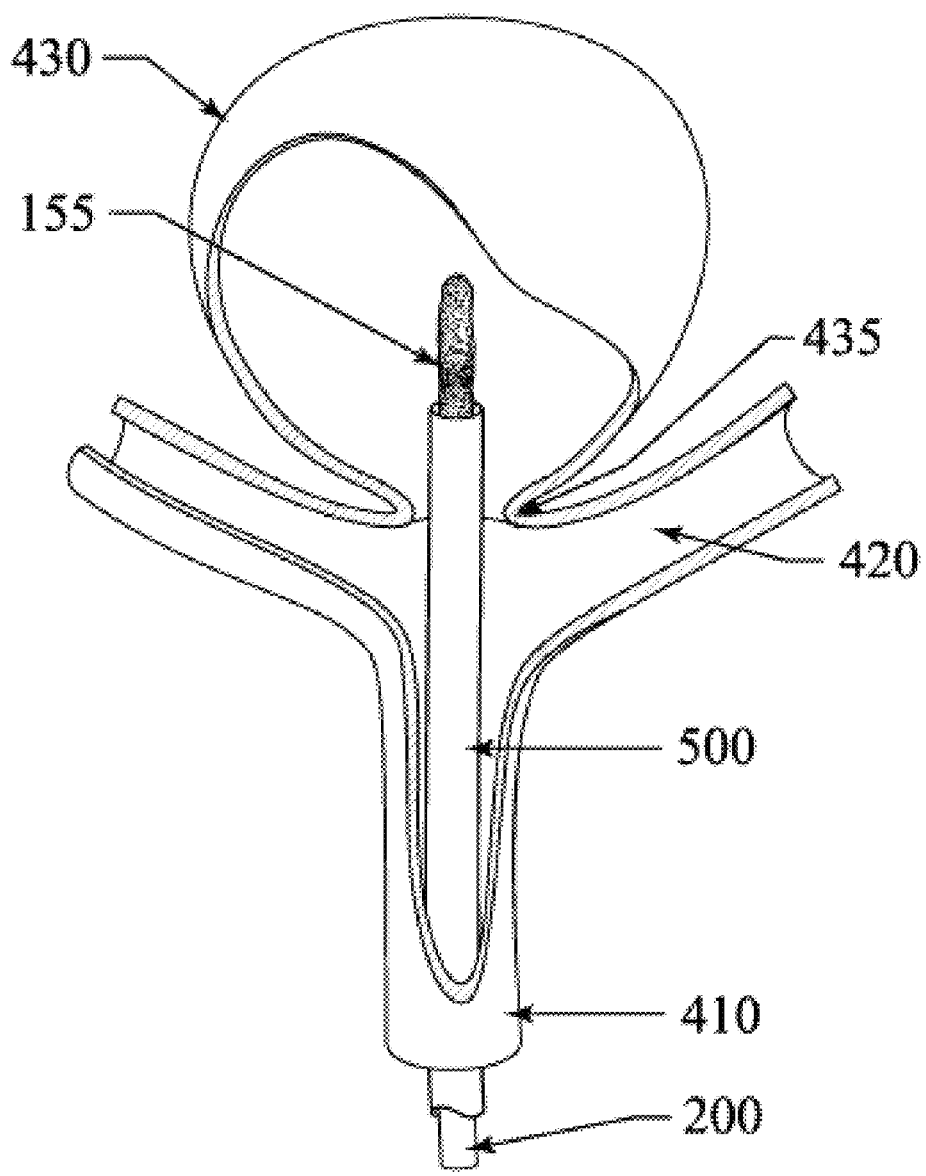
Figure 16:
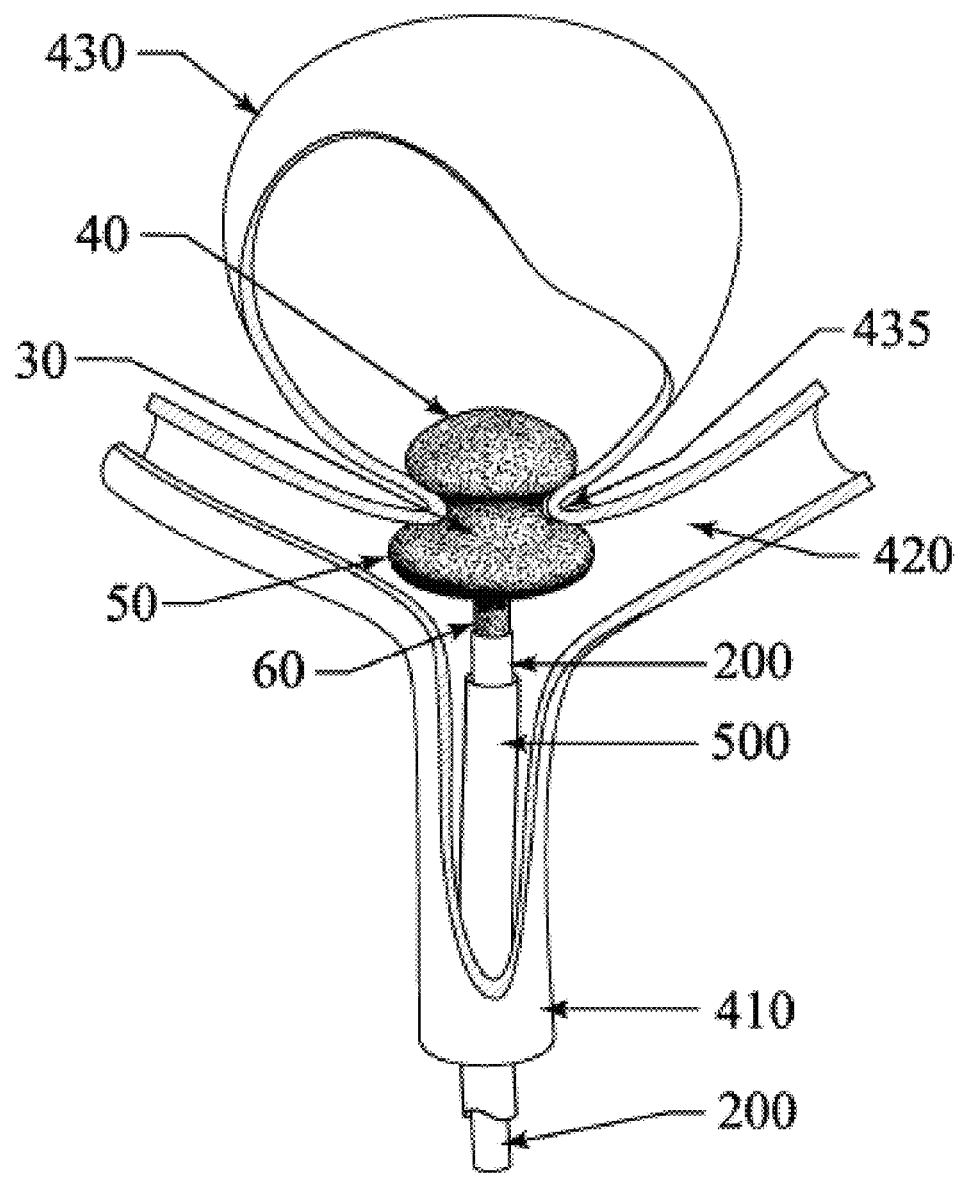

The exclusion device of the present invention is a thin-walled, pressure-vessel shell. The device transitions between an initial as manufactured shape, a compacted shape, a pressure expanded shape similar to the as manufactured shape, an evacuated crushed shape, and a final balloon-contoured shape. The as manufactured shape of the exclusion device 10 is determined by the shape of the sacrificial mandrel 20 as depicted in FIGS. 1 and 9. The compacted shape will vary slightly depending on the chosen compaction method. One preferred compaction option is depicted sequentially in FIGS. 2, 3A, 3B and 3C, which show the exclusion device 10, flattened 110, folded 140, and rolled 150. The exclusion device may alternatively be compacted in a generally radial manner 155, as depicted in FIGS. 4 and 12. Positive pressure transmitted through a delivery tube 200 expands the device 10 to a shape resembling its as manufactured shape, as is depicted in FIG. 5 and 16. Vacuum pressure transmitted through a delivery tube 200 is used to transform the exclusion device to a collapsed shape as depicted in FIG. 6, 7, 17 and 18. A balloon catheter expanded in the parent artery results in final balloon contoured shape as depicted in FIG. 8.

FIGS. 9 and 10 depict an optional configuration of the exclusion device that includes a bellows section 80. The bellows 80 facilitate placement in an aneurysm on the side of an artery as shown in FIG. 10. In FIG. 9 and 10, two lobes are shown in the bellows section but more and smaller lobes may be used.

The delivery tube 200 is designed to accommodate the attachment of the exclusion device shell 10, in an air tight fashion, to its distal end. The balloon-like exclusion device shell 10 includes an aneurysm (distal) lobe 40, a waist 30, and an artery lobe 50.

The device 10 requires some form of compaction for delivery. Several compaction methods have been tested and many other possible methods exist. Flatten, fold, and roll (as depicted in FIGS. 3A, 3B and 3C) compacts the device into a form that opens at a lower pressure. This method, however, may not be compatible with a separate expansion of the aneurysm lobe prior to the full expansion of the device. If flattened, folded, and rolled, both lobes of the device preferably unroll together and expand simultaneously. Rolling may be the most effective method for captivating the guidewire 300, although the guidewire may be captivated in a radially compacted 155 device 10 as well. The compaction method used must be compatible with the planned deployment method.

For deployment, a guidewire 300 is first advanced into the aneurysm 430. Standard angiographic, procedures may be used to view the arteries and aneurysm. The exclusion device 10 is located with its waist 30 in line with the neck 435 of the aneurysm 430. Positive pressure transmitted through the delivery tube 200 expands the exclusion device.

In delivery method option one, as depicted in FIGS. 2-10, the guidewire 300 is outside of the delivery tube 200 and may be threaded through a guidewire guide 220 at the distal end of the delivery tube 200. The guidewire guide 220 reduces stress on the rolled 150, or otherwise compacted 155, device during the delivery process. In this delivery method, the device is preferably flattened 110, folded 140, and rolled 150, around the guidewire 300 as shown in FIGS. 2, 3A, 3B, and 3C. The device may also be radially or otherwise compacted 155, without being rolled 150, around the guidewire 300. Compacting the device around the guidewire 300, without rolling 150, may be necessary if the aneurysm lobe 40 of the device is to be expanded separately from the artery lobe 50. The guidewire 300 slides freely in the tubular channel formed by the rolled 150, or otherwise compacted 155, device 10. A cylindrical, temporary aid may be used to provide a controlled clearance between the guidewire 300, and the compacted exclusion device 150 or 155, during assembly. To deploy the exclusion device, the flexible guidewire tip 310 is first advanced into the aneurysm. In this delivery option one, the device is advanced over the guidewire 300 as the delivery tube 200 is advanced. The rolled 150 or otherwise compacted 155 exclusion device may be located with its waist 30 in line with the neck 435 of the aneurysm 430 as shown in FIG. 4. Positive pressure in the delivery tube 200 expands the device.

In delivery method option two, as shown in FIGS. 11-18, the compacted exclusion device 155 is advanced through an outer catheter tube 500 after the guidewire 300 is removed. Delivery method two may also use an exclusion device that is rolled 150 as a means of compaction, however, the device would not be rolled around a guidewire 300 since with this delivery method, the guidewire 300 is removed before the device is pushed through the outer catheter tube 500. Fluid pressure and fluid flow may be applied at the proximal end of the catheter tube 500 to lubricate and help carry the device 10 and delivery tube 200 through the catheter tube 500. The delivery tube 200, with the device 10 attached to the distal end, is pushed through the outer catheter tube 500 to the deployment site. Unlike delivery option one, the guidewire is not available to stabilize the device position at the aneurysm neck during deployment. When the deployment is generally straight into the aneurysm, as shown in FIGS. 1-8 and 11-18, option two deployment is relatively straight forward. However, where a straight deployment is not possible, as shown in FIG. 10, small catheters with pre-shaped tips or catheters with steerable tips may be used to direct the device into position at the neck of the aneurysm. Bent tip and steerable catheters are known in the art.

An additional option for retaining the catheter tip in the aneurysm after guidewire removal uses a flexible, but straight-tipped, catheter. This method places the tip of the catheter within the aneurismal sac and uses the wall, or neck, of the aneurysm to support the catheter's distal end, retaining the catheter tip in the aneurysm for exclusion device deployment. If a deployment method is chosen where the opening of the catheter is within, rather than at the neck of, the aneurysm, the technique depicted in FIGS. 13-15 with delayed artery lobe expansion would be used.

Figure 13:
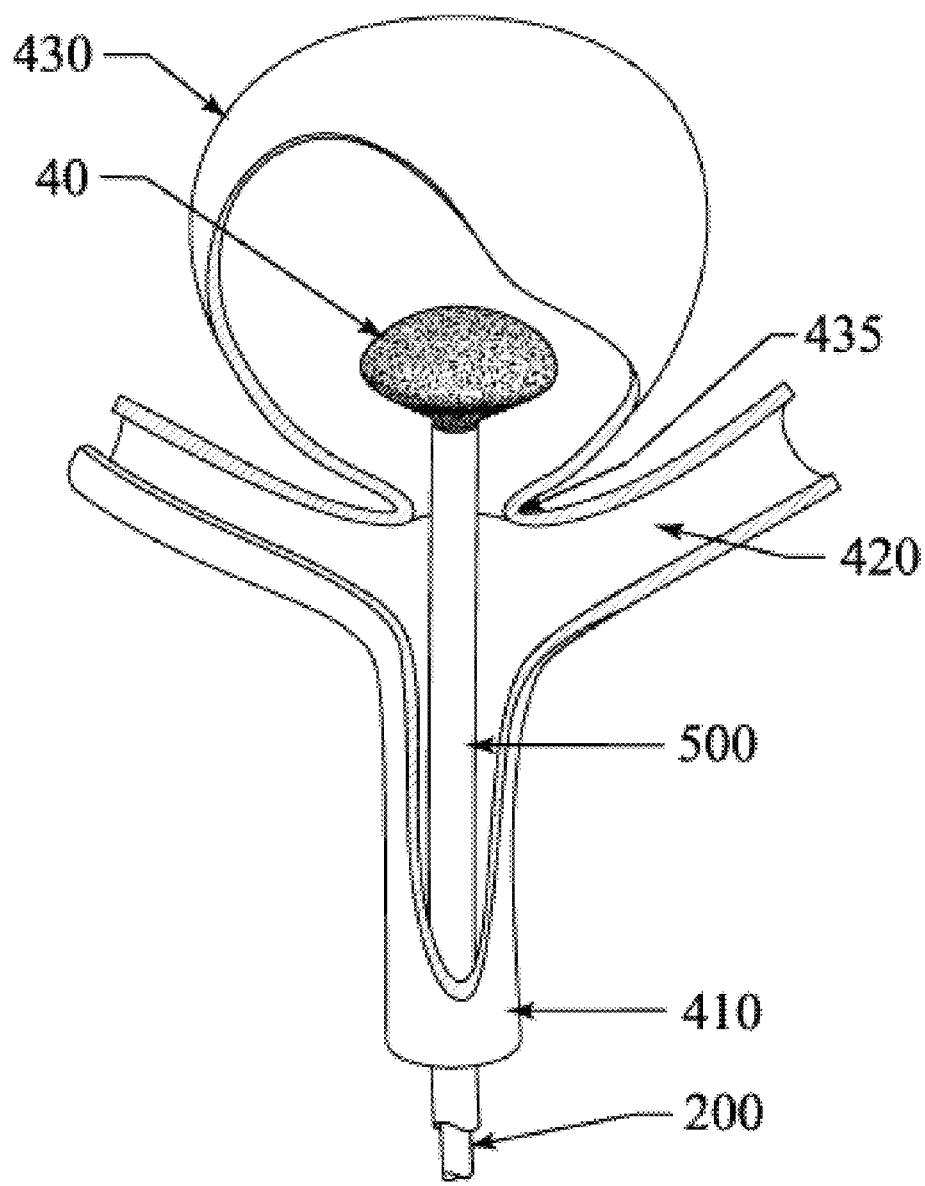
Figure 14:
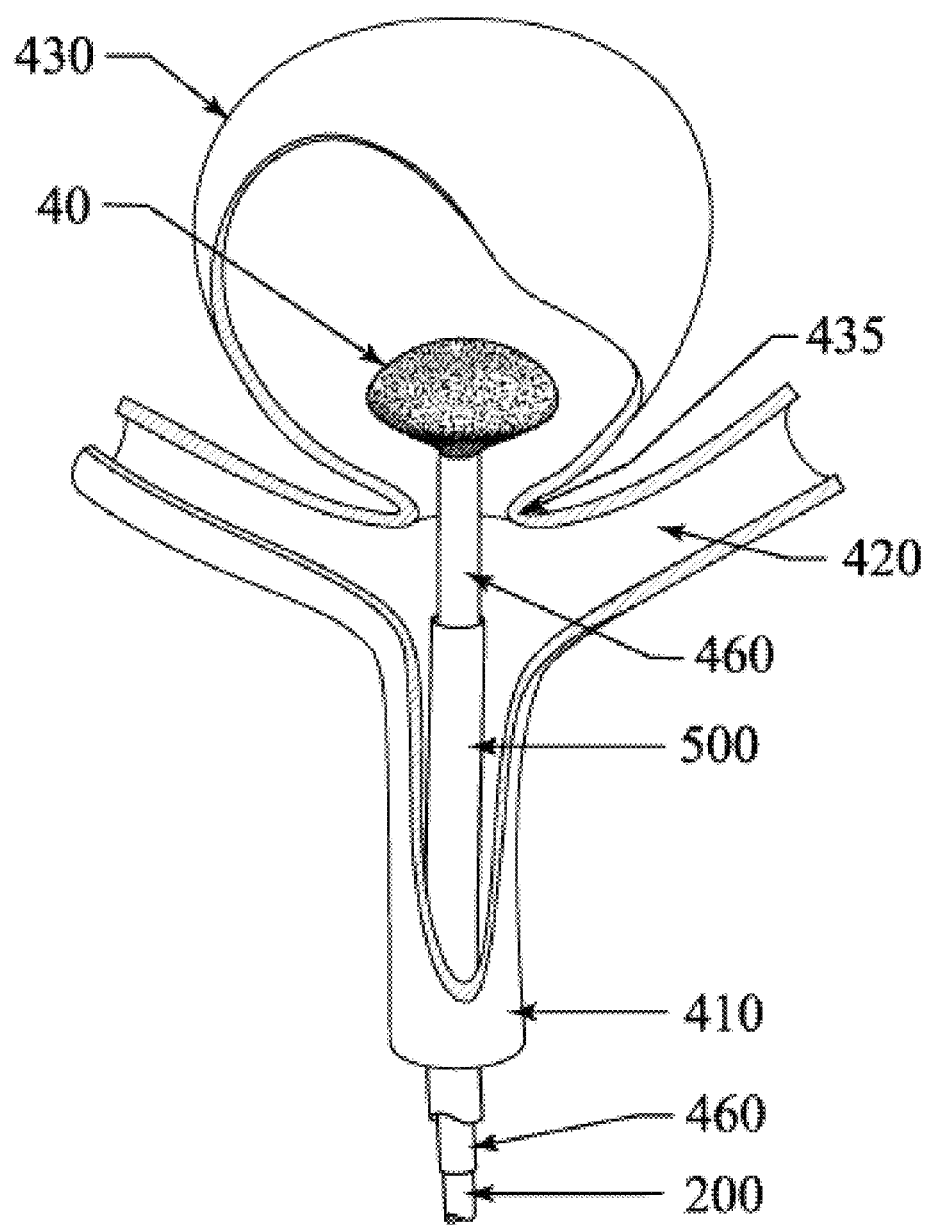
Figure 15:
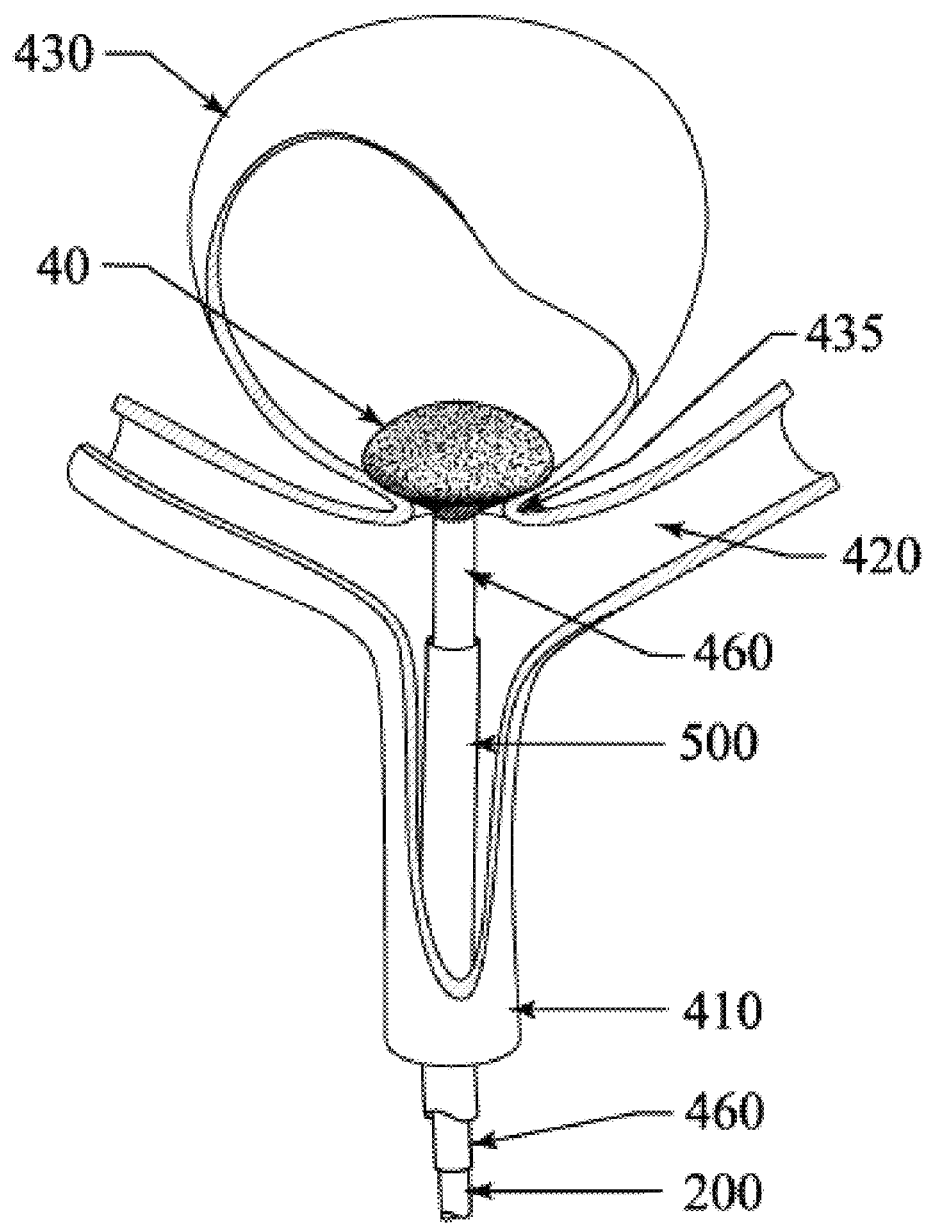

In both delivery methods described above, it may be advantageous to first apply positive pressure into the exclusion device when only the aneurysm (distal) lobe 40 and waist 30 of the exclusion device are free to expand (as shown in FIGS. 13-15). To accomplish this technique, the artery lobe 50 may be restrained as the aneurysm lobe 40 is expanded. In delivery method one, since there is no outer catheter tube 500, a protective sheath 460, or another method, could be used to restrain the artery lobe. In delivery method two, either the protective sheath 460 or the outer catheter tube 500 may be used as a means of restraining the artery lobe (as shown in FIGS. 13 and 14). This allows the expanded aneurysm (distal) lobe 40 to hold the device in the aneurysm (as shown in FIG. 15), while the outer catheter tube 500, or protective sheath 460, is pulled proximally, releasing the artery lobe 50 of the device. When the sheath 460, or outer catheter tube 500, is pulled proximally a sufficient distance from outside the body, the device is unconstrained and in position for full expansion and subsequent collapse. The cylindrical portion of the protective sheath 460 may be only long enough to cover the exclusion device, and string, or strings, which may be connected operably to the cylindrical section, and may extend to the outside of the body to facilitate controlled pull back of the sheath. If necessary, the pressure in the device could be reduced slightly before the outer catheter tube 500, or protective sheath 460 (if used), is slid off of the artery lobe 50 of the exclusion device. Additionally, the sheath 460 may function to protect the exclusion device and reduce friction during movement within the catheter 500. Other methods may be used to insure that the aneurysm lobe 40 expands before the artery lobe 50. For example, the artery lobe may be thicker or more tightly compacted to insure that the aneurysm lobe 40 opens first, at a lower pressure.

If using delivery method one, the guidewire 300 would be removed from the aneurysm (as shown in FIG. 5 and FIG. 10) before the exclusion device is fully expanded. If using delivery method two, the guidewire 300 may be removed from the aneurysm after the outer catheter tube 500 is in place within, or just outside, the aneurysm neck but before the device is fully expanded—or alternatively, before the device is pushed through the outer catheter tube 500.

Figure 6:
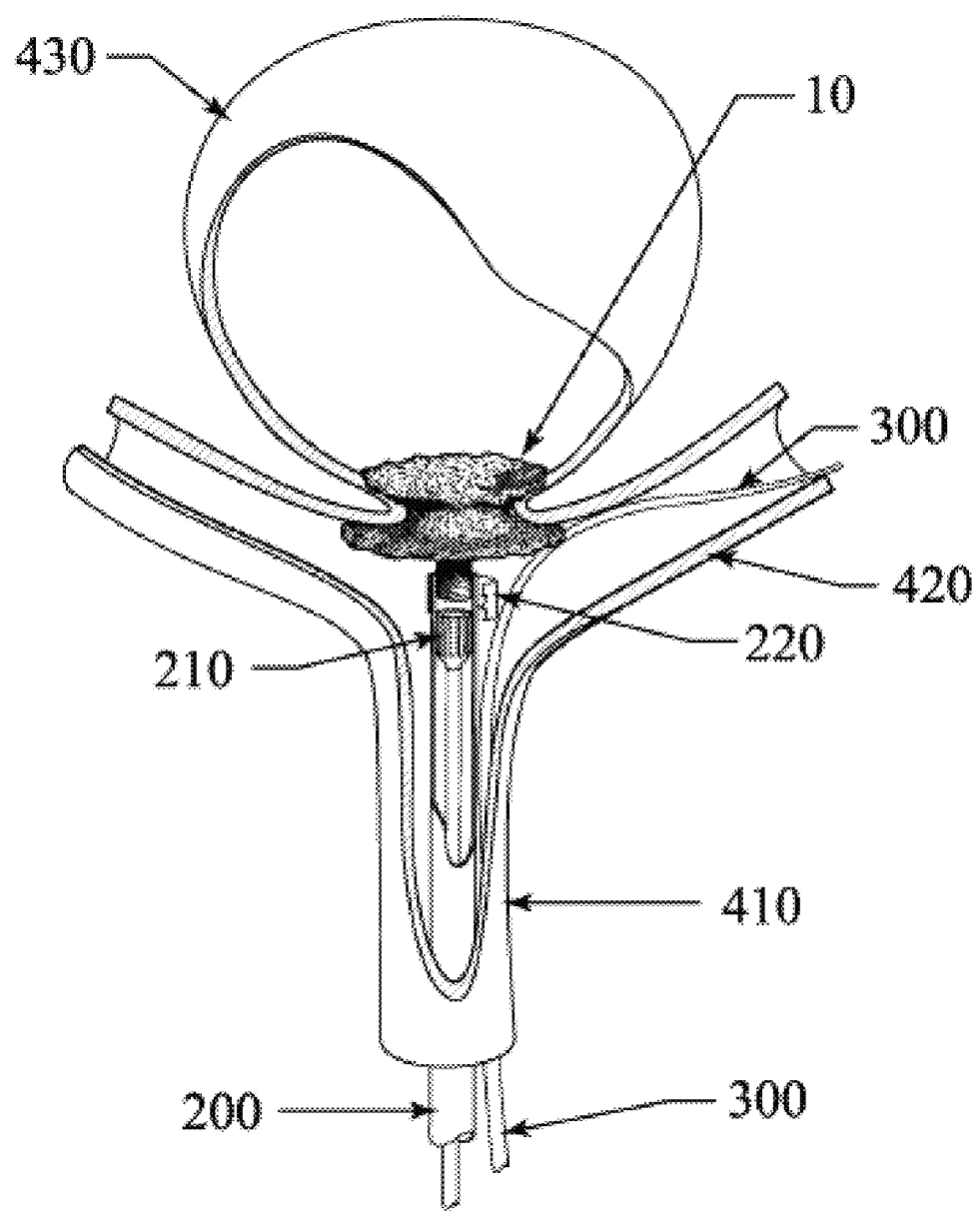
Figure 7:
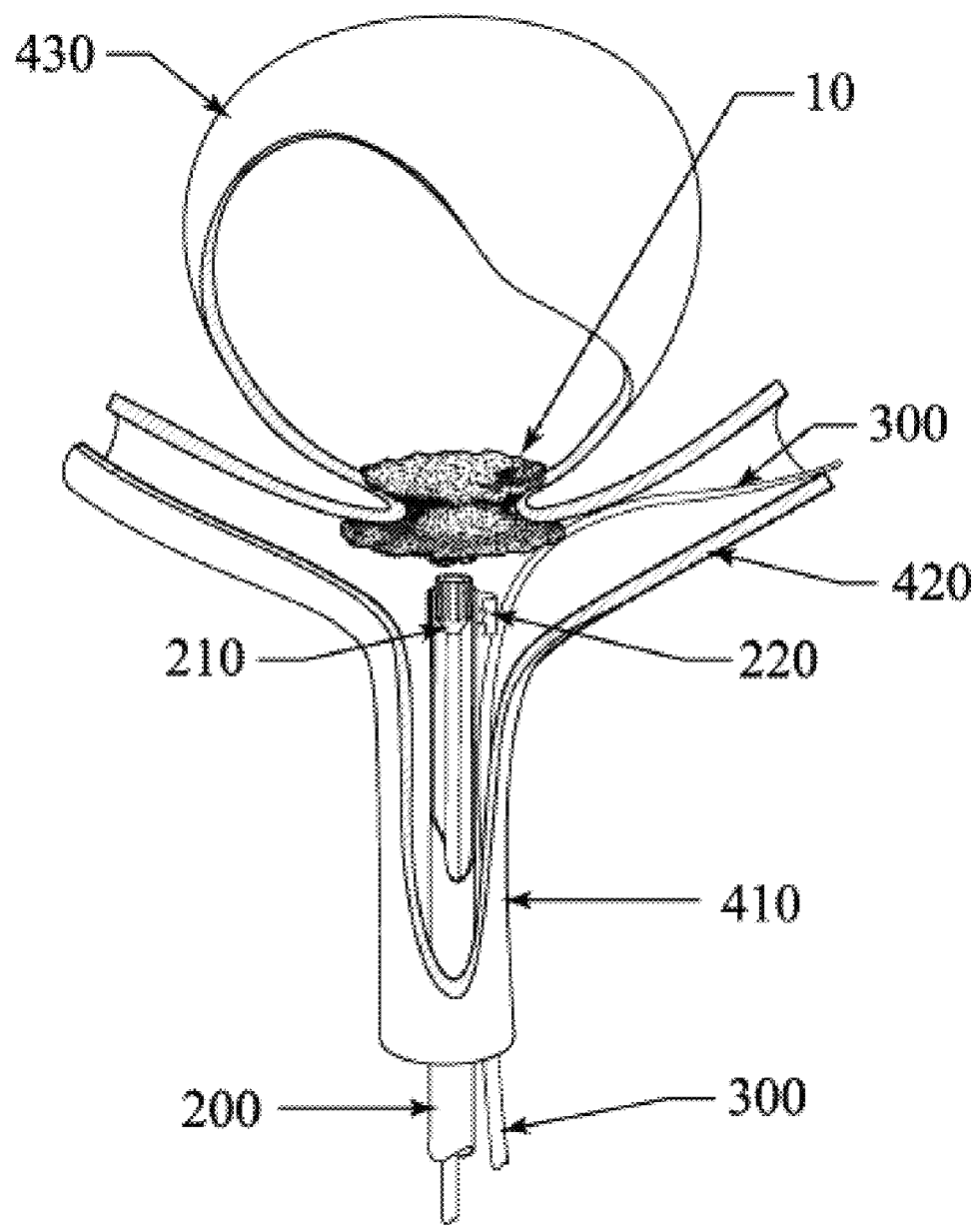
Figure 17:
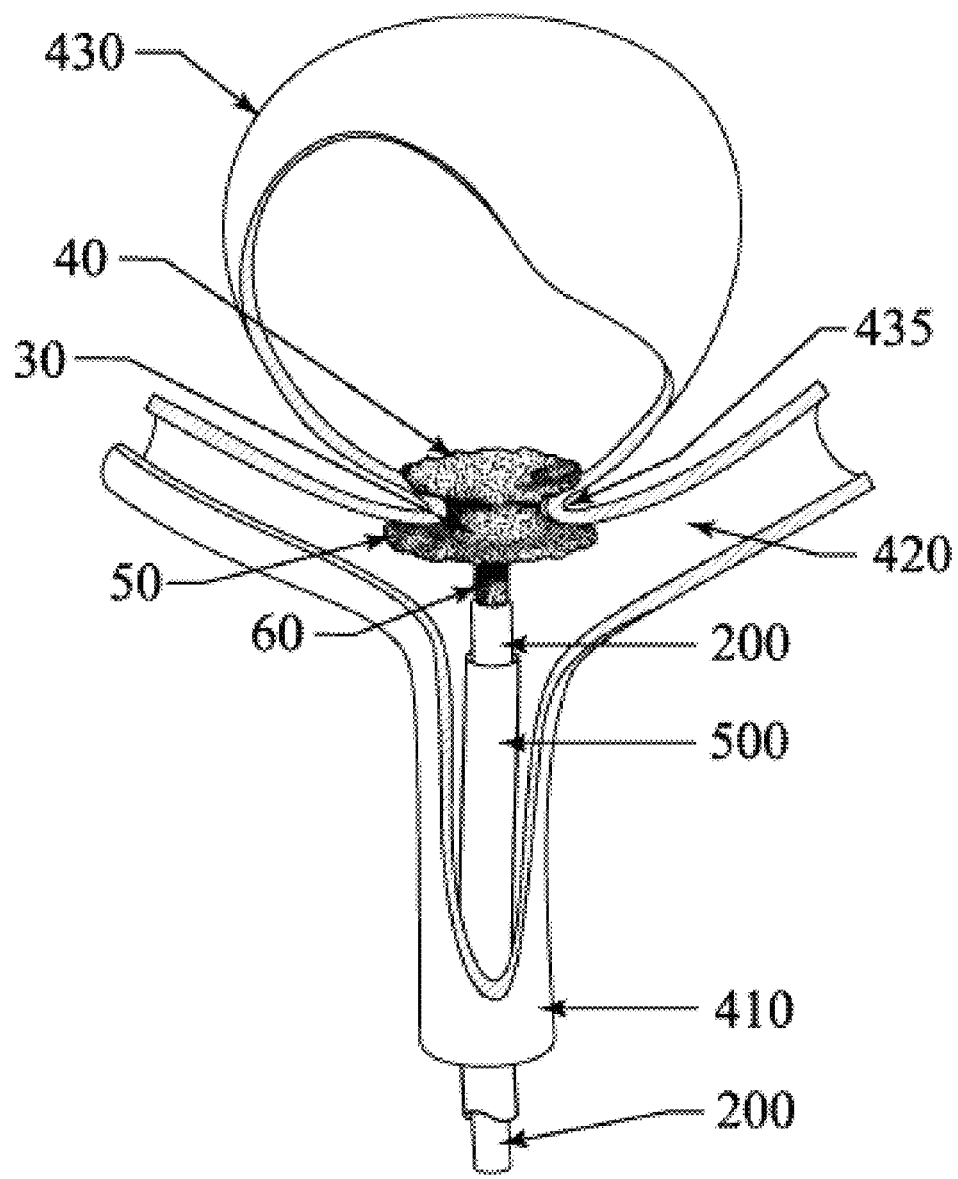

After the exclusion device is positioned and expanded (as shown in FIG. 5 and 16), the device subsequently is collapsed by applying vacuum pressure through the delivery tube 200 (as shown in FIG. 6 and 17). External pressure collapses the two lobes of the exclusion device, captivating the neck 435 of the aneurysm between the two collapsed lobes.

The exclusion device may be disconnected from the delivery tube 200 in a variety of ways, many of which will be, or will become, apparent to those skilled in the art. The disconnection options described here are applicable to either delivery method one or two. One option to disconnect the exclusion device from the delivery tube 200 involves advancing a pushed wire 210 inside the delivery tube and shearing the exclusion device from the delivery tube. Another option simply rotates the delivery tube, shearing off the stem of the device in the process.

Figure 18:
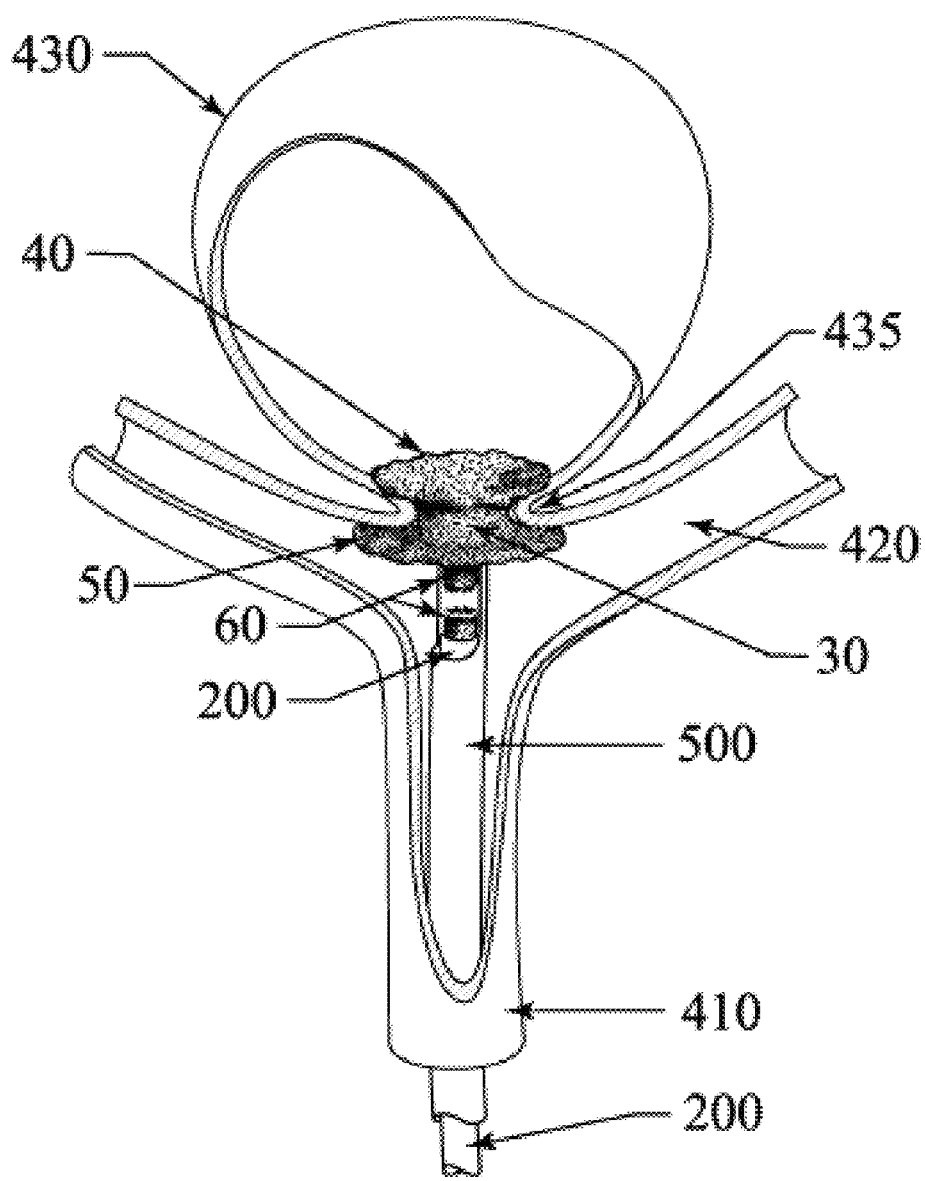

Another method for disconnection uses a catheter tube 500 outside the delivery tube 200 to shear off the deployed exclusion device shell near its stem, freeing the device from the delivery tube 200 as shown in FIG. 18. For this method, the distal tip of the protective sheath 460 or the distal tip of the outer catheter 500 could be used to shear the device shell where the stem 60 connects with the proximal lobe 50 of the device 10. The outer tube will be maintained in place to hold the collapsed shell in place while the delivery tube 200 is pulled back to shear the thin shell material and disconnect the device 10 from the delivery tube 200.

Other disconnection systems using electrochemical dissolution or heat to remove or destroy an element in the connection chain may be used. After disconnection of the exclusion device, the delivery tube 200 and the disconnection pusher wire 210 are removed from the body. The final step in the deployment (as shown in FIG. 8) of the exclusion device advances a standard balloon catheter 600 over the guidewire 300. The balloon at the distal end of the catheter is located, and expanded, pushing any portions of the artery lobe 50 and stem 60 of the exclusion device 10 against the artery wall, flattening the device and fully opening the artery. Multiple balloon expansions may be necessary, especially when the aneurysm is located at a bifurcation. If the exclusion device is constructed from a thicker, or stiffer, material, it may be impossible to collapse the exclusion device with available negative pressure. In this case, the aneurysm lobe may be left in the expanded state, and the artery lobe may be collapsed and then contoured using a balloon catheter.

The following description elucidates, with varied characteristics, the general steps, and options, in the design, and manufacturing, of exclusion devices and the situations where the present invention may be used.

It is anticipated that a number of shapes, and sizes, of exclusion devices would be manufactured for various applications. The range of types, and shapes, of the exclusion device would be determined by the needs of each particular application. The device may be constructed from rubber, plastic, PARYLENE™, gold, platinum, or other ductile metals, singularly, or in combinations.

When using the exclusion device to exclude an aneurysm from the circulatory system, the appropriate waist 30 diameter of the exclusion device 10 would be approximately 1 mm smaller than the neck 435 of the aneurysm requiring treatment. The diameters of the two lobes may be approximately 2 mm larger than the neck 435 of the aneurysm. The two lobes need not be symmetrical; each lobe's respective shape, and sizes, is variable and determined by the design, and machining, of an appropriate mandrel.

The stem 60 design, and opening size, are also variable. In order to facilitate an air tight, and appropriately strong, seal between the delivery tube 200 and the exclusion device stem 60, the stem 60 size, including length and diameter, will be based upon the size, and design, of the delivery tube 200. If the stem is to be glued to the inner wall of the delivery tube, the diameter for the stem 60 of the mandrel 20 will be equal to the inside diameter of the delivery tube 200, minus two times the thickness of the device wall. If the device is formed by electroplating, extra stem 60 length will be left on the mandrel for electrical connection. Excess stem 60 length will be removed after electroplating in order to expose the mandrel 20 for dissolving. If coating the mandrel with plastic or other non-electroplated material, the excess coating and stem will be trimmed to the final stem length, exposing the mandrel for removal.

The mandrel material must possess appropriate physical characteristics including, but not limited to, the ability to be machined into the desired shape and sacrificially dissolved within the exclusion device shell. Brass and copper have been found to work well with gold, platinum, and PARYLENE™ exclusion shells. The mandrel may be fabricated on a computer controlled lathe.

In preparation for electroplating, a metal stem extension is soldered onto the stem of the mandrel. The extension provides both an electrical contact and a mechanical support for the mandrel in the electroforming bath. Next, a resist mask is applied over the solder joint, forming a band of resist that controls plating at the area, restricting plating specifically to the mandrel and the portion of its stem not covered by resist. The resist band allows plating slightly beyond the final stem length. The stem extension, with attached mandrel, is then placed vertically into a plating bath to a depth that covers the mandrel and a portion of the stem extension. This alignment is accomplished by aligning the surface of the bath with the resist band.

Using the standard electroplating techniques, gold, or other metals, is electroformed on the mandrel. Typically, the mandrel is rotated about its axis during plating. Exclusion devices of the present invention, designed to treat neurovascular aneurysms, typically have an electroplated metal shell between 3 and 10 microns thick. For larger devices, the electroplated metal thickness can be increased accordingly. The thickness, design, material, and material properties of the exclusion device may be modified in order to allow collapse of the exclusion device with a vacuum.

After electroplating, the excess stem is trimmed by excising the stem extension below the solder joint and grinding excess material to the designed stem length.

In order to dissolve the sacrificial mandrel, a dissolving liquid needs to be introduced into the stem of the exclusion device and circulated throughout the exclusion device. One method for removing the mandrel uses vacuum cycling, with controlled pressure ramps, to circulate the dissolving liquid into the shell through the stem by controlled expansion and contraction of gas generated as the mandrel dissolves.

The following example uses gravity to create the fluid exchange inside the exclusion device. If a Copper or Brass mandrel is used, an appropriate reservoir is filled with 500 ml of dissolving liquid, ⅓ strength (by volume) nitric acid ($HNO_3$). If the mandrel is constructed from a different material, a liquid known to selectively dissolve that mandrel material should be used.

With stem facing up, the mandrel is placed in a TEFLON™ fixture. The fixture, and mandrel, are placed in a catch basin, composed of material suitable for containing the dissolving liquid. A stainless steel hypodermic needle is connected to a TYGON™ tube that is in turn connected to a reservoir containing the dissolving solution. The needle is then placed in the fixture directly above the exclusion device stem. The reservoir is elevated an appropriate distance above the needle in order to facilitate the use of gravity to obtain the correct pressure to create the desired rate of flow.

After a sufficient amount of the mandrel has been dissolved, the needle is lowered into the stem so that the dissolving liquid flows into the interior of the exclusion device shell. The initial mandrel removal from the stem, however, could be accomplished by immersion of the exclusion device in a container of the dissolving liquid. Once the stem is partly open, the needle is placed in the stem to complete the mandrel removal.

When gas evolution from the shell has ended, the shell is cleaned and dried. One rinsing option leaves the needle in place in the shell, with the tubing connected to a high-purity water reservoir that circulates water into the mandrel. Other methods may be used provided that a minimum volume of high purity water equal to about 100 times the volume if the shell is passed through the mandrel free shell.

Next, with the exclusion device stem pointing down, the tubing may be connected to a low-pressure dry-air supply (3 psig) in order to remove all excess water from the exclusion device shell, completely drying the shell. This rinsing and drying process may be accomplished in any functional manner known to those skilled in the art. The water rinse and air purge procedures should be repeated at least two times. The metal exclusion device shell can then be dried in an oven at approximately 110° C. To increase the ductility of a metal exclusion shell, the shell may be annealed in a high temperature oven. For example, a gold shell should be annealed at temperature between about 200° C. and about 500° C.

A porous surface layer for storage and elution of substances including, but not limited to, drugs, proteins, cells, genetic material, living tissue, and/or growth factors, etc. could be added to all, or part, of the device using the methods of U.S. Pat. No. 6,904,658 (PROCESS FOR FORMING A POROUS DRUG DELIVERY LAYER to Richard A. Hines). The porous layer could be used to improve endothelization with, or without, delivery of a substance. A porous layer of this method could be used to deliver biological material(s) in addition to, or in place of, a drug.

The entire exclusion device could be manufactured with varying degrees of porosity by producing an exclusion device with either small or large holes. If the holes are small, the shell may be pressure expanded and collapsed without the need to plug the holes. The porous exclusion device shell, with either small or large holes, could be covered, or painted, with a material that would plug the manufactured holes. After deployment in the body, the plug material would dissolve at a predetermined rate, leaving a mesh-like shell in the artery that would facilitate rapid migration of tissue cells through, and across, the surface of the exclusion device to improve endothelization.

An exclusion device with small holes, typically between 5 and 25 microns, could be manufactured using high-current electroplating and would allow the shell to expand and collapse in the inventive manner previously described.

Larger holes, typically between about 25 and 100 microns, could be useful in assisting the endothelization of arterial tissue to the exclusion device. An exclusion device manufactured with larger holes could use dissolvable, or biodegradable, plugs that enable pressure to expand and collapse the exclusion device. A porous shell with large holes would still sufficiently reduce flow into the aneurysm to trigger a thrombus in the aneurysm and start the healing process.

Various methods could be employed to produce an exclusion device with large holes. The exclusion device could be a woven mesh-shape over the mandrel. The porous shell net could be formed from gold, or another suitable, wire or fiber materials. One method could form a porous shell by employing heat, and/or pressure, to bond fibers over a mandrel. The wire shell could be woven, or knitted. Photoimaging and electroforming—as taught in U.S. Pat. No. 6,019,784 (PROCESS FOR MAKING ELECTROFORMED STENTS to Richard Hines) and U.S. Pat. No. 6,274,294 (CYLINDRICAL PHOTOLITHOGRAPHY EXPOSURE PROCESS AND APPARATUS, also to Hines)—could be used to produce the large holes.

Laser exposure, or a clam shell mask, could also be used to selectively expose photoresist onto the exclusion device that, after development, would leave spots of resist, thereby creating holes in the electroformed shell. Complete shells could be electroformed and then laser drilled to produce the holes. A thick, electroformed shell could be laser drilled and then cut in half to create the clam shells for resist exposure.

In yet another method, photoresist could be sprayed, in a non-continuous layer, onto the device, creating spots of resist that would form holes in the electroformed shell.

The entire exclusion device, or parts thereof, may be manufactured from dissolvable, or biodegradable, materials. For purposes of this specification, "dissolvable" is defined as a substance that changes from a solid to a form with greater disbursement when placed in contact with the fluids of the body, and "biodegradable" is defined as a substance that is chemically degraded, or decomposed, when placed in contact with the fluids of the body.

For example, a shell with larger holes could be manufactured from a material that biodegrades within a time period ranging from a few days to a few months, and the holes in the shell could be filled with a similar, or different, material that dissolves or biodegrades at a quicker rate, on the order of a few minutes to several days, than the material used to manufacture the shell. The material used to fill the holes in the shell is needed to maintain the pressurized vessel functions for both expansion and collapse of the exclusion device. Aneurysm treatment research indicates that in a post-deployment environment the exclusion device must maintain a minimum of only 30% solid coverage over the neck of the aneurysm. These parameters, of course, may vary slightly depending upon the intended use of the exclusion device. Following deployment, the dissolvable or biodegradable portions would separate from the exclusion device and safely enter the blood stream. The remainder of the exclusion device could either remain permanently in the aneurysm or biodegrade and/or dissolve completely after a predetermined period of time. Once a thrombus is formed in the aneurysm, and an appropriate amount of endothelial tissue has grown over the neck of the aneurysm, the exclusion device has accomplished its purpose. If the exclusion device is manufactured from a biologically inert material, it may be left encapsulated in the endothelial tissue, or if the exclusion device is manufactured from a biodegradable material, its design facilitates gradual degradation, or absorption, in whole, or in part. Any combination of biodegradable, dissolvable, or permanent material(s) could be used within the scope of this invention to manufacture the exclusion device.

To allow stem flexibility for delivery of the exclusion device 10 into an aneurysm 430 located on the side of an artery 410, one embodiment of the present invention (FIGS. 9 and 10) includes bellows 80 formed in the stem 60. If the aneurysm position is such that a straight outer catheter tube would tend to spring, or fall, out of the aneurysm once the guide wire is removed from the aneurysm, an outer catheter tube 500 with a pre-shaped end could be used, and the tip, or some distal portion of the outer catheter tube, could be placed within the aneurysm, with a point on the distal portion resting against the wall, or neck, of the aneurysm. In situations where the distal end of the outer catheter tube is actually contained within the aneurismal sac, rather than at the neck of the aneurysm, it would probably be necessary to use the device deployment method depicted in FIGS. 15 and 16, inflating the aneurysm lobe separately, and prior to, the artery lobe expansion.

A liquid agent, with or without radiopacity, could be used to fill, expand, and collapse the exclusion device. A liquid agent, or fill material, that solidifies after exclusion device collapse and balloon contouring could aid in establishing the final exclusion device shape. This liquid agent would be particularly useful in PARYLENE™, or plastic, shelled exclusion devices. Additionally, the inside surface of the exclusion device, particularly if the exclusion device is constructed from PARYLENE™, plastic, or with a plastic inner lining, could be activated by a solvent, or other solution, after placement, and expansion, within the body, creating a tacky inner shell that causes the shell to stick to itself when vacuum collapsed and balloon contoured.

The exclusion device, and associated assembly, is designed for intraluminal delivery. The design characteristics of the invention allow the exclusion device to be compacted to an exceptionally small size and be more flexible during, and effective upon, delivery than previously disclosed aneurysm neck-covering devices. In particular, the device may be manufactured, and delivered, as described herein in such a way that enables use in the tiny, tortuous, and complex neurovascular anatomy. The numerous unique benefits, including the degree of safety, accuracy, and reliability in which this exclusion device can be realistically delivered deep into the tortuous arteries of the brain, make it both novel and useful.

In both of the two general delivery methods described herein, the exclusion device is connected, in an airtight fashion, to the distal end of a delivery tube 200. Depending upon the choice of disconnection method, the exclusion device stem 60 may be slid into, or over, the distal end of the delivery tube and then glued into place. Medical grade LOCTITE™ 4011 has been used to successfully glue the exclusion device to the delivery tube. The strength of the glue joint must be sufficient to allow pressurization, and evacuation, of the device but delicate enough to be easily broken when the detachment pusher 210 is advanced to detach the exclusion device. However, the glue joint should be extremely strong if disconnection of the shell requires shearing of the shell while leaving the glue joint intact. Other methods, apparent to those skilled in the art, may be applied to leak-test the exclusion device and its connection to the delivery tube.

In delivery option one, an optional guidewire guide 220 may be used as part of the delivery system. The guidewire guide 220, consisting of a thin-walled tube, or ring, manufactured from a material with a low coefficient of friction to the guidewire, would be attached to the delivery tube 200 near the distal tip of the delivery tube. The axis of the guidewire guide is parallel to the delivery tube and extends as a thin-walled cylinder beyond the tip of the delivery tube to a distance equal to, or less than, the distance that the waist of the exclusion device extends beyond the distal tip of the tube. The guidewire guide reduces stress on the rolled exclusion device by holding the guidewire adjacent to the delivery tube. The thin-walled cylinder that extends beyond the catheter tube reduces possible damage to the exclusion device, damage that could result from the relative movement between the rolled exclusion device and the guidewire as the exclusion device is advanced over the guidewire and into the aneurysm. To prevent entrapment in the aneurysm when the exclusion device is expanded, the thin-walled cylinder should not extend beyond the waist of the exclusion device.

Figure 2:
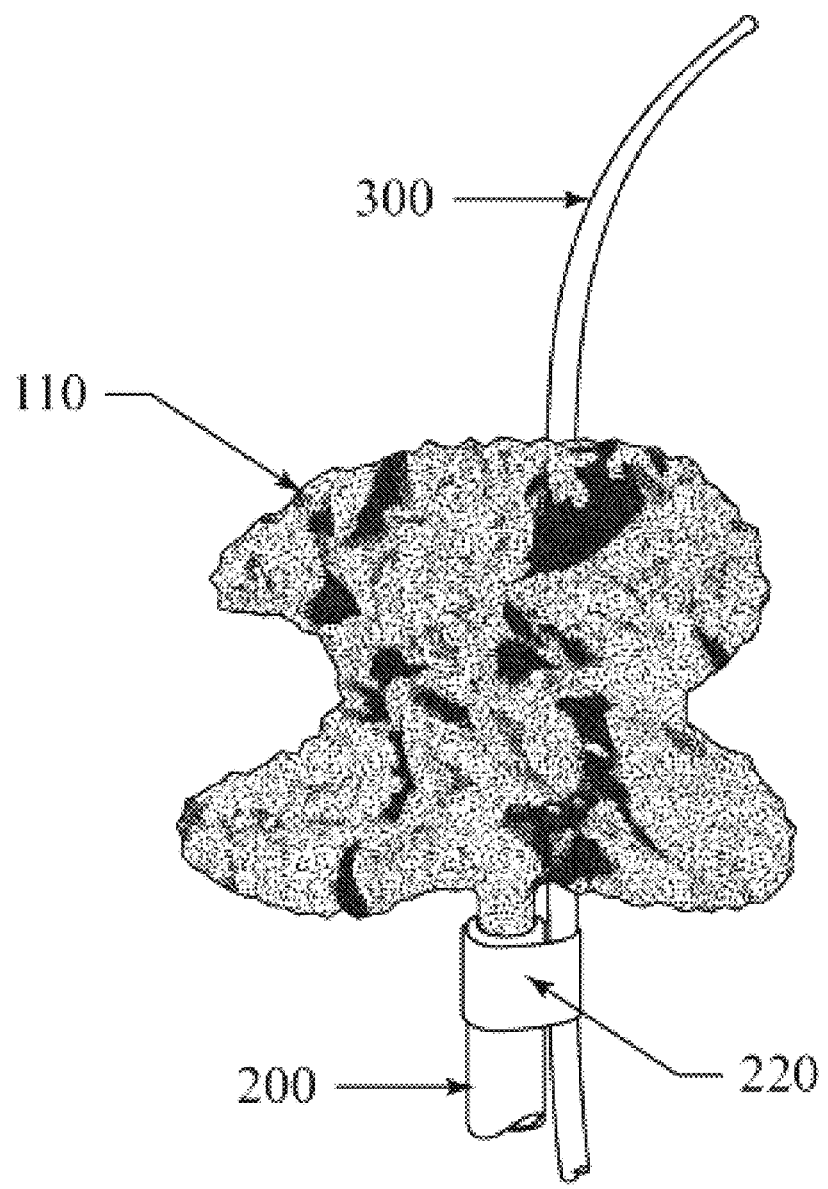

In delivery option one, the exclusion device is first gently flattened, forming wrinkles and folds in the shell (as shown in FIG. 2). The flattened exclusion device shell 110 is then folded, and rolled, around the guidewire 300 (FIG. 3A, 3B, and 3C).

In both described delivery options, the guidewire is first advanced into the aneurysm in a standard fashion. In the first delivery option, the outer catheter tube is then advanced over the guidewire to a position just inside of the aneurysm. In either delivery method, an optional guide-catheter may be used to facilitate advancement of the exclusion device to a predetermined point in the neurovascular anatomy close to the site of the aneurysm.

In delivery option one, the exclusion device is advanced over a guidewire and into the aneurysm. If the aneurysm lobe 40 is to be expanded first, and separately, exact positioning is not crucial, provided that the lobe is expanded within the aneurysm. If both the aneurysm lobe 40 and the artery lobe 50 are to be expanded simultaneously, the neck of the exclusion device should be aligned approximately with the neck of the aneurysm 435. The novel device geometry, material properties, and controllable low-pressure inflation-based deployment system, provide self-alignment of the waist of the exclusion device within the neck of the aneurysm. A standard syringe pump may be used to increase the pressure in the exclusion device, causing it to unroll. Prior to pulling back the catheter and completing the expansion, the exclusion device may be partially extended from the outer catheter in order to expand the aneurysm lobe, but before fully expanding the exclusion device, the guidewire 300 should be removed from the aneurysm, leaving the tip of the guidewire 310 in the artery, distal to the aneurysm, so that it will be ready to guide a balloon catheter 600 to the site of the aneurysm. With the guidewire removed from the aneurysm, a contained increase in pressure within the exclusion device will fully expand the exclusion device to its as-manufactured shape. As the device expands, its shape will tend to auto align the waist of the device with the neck of the aneurysm.

Minor adjustments in the outer catheter tube positioning may be necessary in order to obtain the desired position of the exclusion device. When positioned properly, the expanded distal lobe of the device will be completely inside the aneurysm, the expanded proximal lobe inside the artery, and the waist of the device aligned with the neck of the aneurysm.

Next, the exclusion device shell should be evacuated and collapsed. The design of the exclusion device ensures that external pressure collapses the exclusion device longitudinally, flattening both the aneurysm and artery lobes in a plane perpendicular to the axis of symmetry. A standard syringe pump, or other method apparent to those skilled in the art, may be used to evacuate the exclusion device. As the pressure is reduced below atmospheric pressure, the device collapses. By reducing the pressure to a minimum, the exclusion device fully collapses and locks itself into the neck of the aneurysm.

Any of several existing, or discovered, methods may be used to disconnect the exclusion device from the delivery tube. Additionally, either of two device-specific novel disconnection methods may be used. In one novel method, the exclusion device stem 60 is attached to the inner diameter of the delivery tube 200, and while the delivery tube 200 is held in position, a disconnection wire 210 is advanced through the delivery tube until it contacts the glue-joint where the exclusion device stem 60 is attached to the delivery tube 200. As the disconnection wire 210 is slowly advanced, the stem/delivery tube joint is severed. In a second novel disconnection method, the stem/delivery tube joint remains intact. The shell is sheared near the stem 60, and the stem 60 and glue-joint are removed from the body. This method is accomplished by using an outer tube 500, or sheath 460 (with the necessary compressive strength), outside of the delivery tube 200. While the outer tube 500 is held in stable position, in contact with the proximal surface of the device 10, delivery tube 200 is pulled proximally, as shown in FIG. 18. This shearing may also be accomplished by holding the delivery tube 200 in stable position, while the catheter tube 500 is advanced distally. The tip of the outer tube 500 easily shears the thin, ductile shell. The tip parameters of this "shearing" tube may be altered depending on the thickness, and type, of the material used to manufacture the exclusion device shell. This method removes the part of the shell material that is glued to the delivery tube 200, and the glue, leaving only the exclusion device material in the body. With minor design modifications still within the scope of this invention, other disconnection systems using electrochemical dissolution, or heat, to remove, or destroy, an element in the connection chain may be used.

Following successful placement of the exclusion device, the delivery tube and detachment wire are disconnected from the device and removed from the body. To shape the device to its final deployed position, the previously collapsed artery lobe may be balloon contoured, tightly conforming it to the arterial wall 420. This technique advances a balloon-catheter 600 over the guidewire 300 to the portion of the artery that contains the aneurysm. The position of, and pressure inside, the balloon may be adjusted during single, or multiple, balloon expansions. The balloon gently forces the section of the exclusion device, which may be partially obstructing the lumen, to the arterial wall. This device contouring technique is uniquely possible with the device of the present invention due to the novel physical characteristics of the device, including, but not limited to, its thin ductile wall.

With some material and thickness compositions used to manufacture the exclusion device, it may not be collapsible with available negative pressure. In this case, the aneurysm lobe may be left expanded, and the artery lobe could be collapsed, and flattened, using the balloon catheter. Following collapse and flattening of the exclusion device, the balloon is deflated and removed from the body.

The outer catheter 500 tip may have at least one radiopaque marker to assist in positioning the exclusion device as it is pushed by the delivery tube, though the outer catheter, to the deployment site. A metal exclusion device with a shell at least 5 microns thick is radiopaque and clearly visible using standard detection procedures. Radiopaque markers may also be applied to the protective sheath 460 if used during delivery.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be constructed to include alternative embodiments to the extent permitted by the prior art.

What is claimed is:

1. A method of delivering an endovascular exclusion device to a treatment site in a body lumen, the method comprising:
   providing a compacted endovascular exclusion ductile metal shell comprising a stem;
   attaching a delivery tube to the stem of the endovascular exclusion shell, wherein the attachment is an airtight connection;
   advancing the delivery tube to a treatment site via a body lumen;
   applying positive pressure via the delivery tube to expand the endovascular exclusion shell in the treatment site; and
   disconnecting the endovascular exclusion shell from the delivery tube; thereby delivering the endovascular exclusion shell to the treatment site in a body lumen.

2. The method of claim 1, wherein the treatment site is an aneurysm.

3. The method of claim 1, wherein the positive pressure is fluid pressure.

4. The method of claim 1, wherein the delivery tube comprises at its distal end an inside disconnection wire, and wherein the inside disconnection wire shears the exclusion device shell from the delivery tube.

5. The method of claim 1, wherein the delivery tube is adapted to accommodate an additional delivery mechanism selected from the group consisting of an outer catheter, a guidewire, a cylindrical sheath, and a combination thereof.

6. The method of claim 1, wherein the endovascular exclusion shell is a mesh-like wire shell or an electroplated metal shell.

* * * * *